US012582486B2

(12) United States Patent
Ruppersberg et al.

(10) Patent No.: US 12,582,486 B2
(45) Date of Patent: Mar. 24, 2026

(54) CONTROLLED CONSTANT CURRENT SYSTEMS, DEVICES, COMPONENTS AND METHODS FOR NAVIGATING, POSITIONING, AND/OR IMAGING A MEDICAL DEVICE INSIDE A PATIENT'S BODY

(71) Applicant: Boston Scientific Scimed, Inc., Maple Grove, MN (US)

(72) Inventors: Peter Ruppersberg, Blonay (CH); Philip Haeusser, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 229 days.

(21) Appl. No.: 18/388,796

(22) Filed: Nov. 10, 2023

(65) Prior Publication Data

US 2025/0152250 A1 May 15, 2025

(51) Int. Cl.
| | |
|---|---|
| *A61B 34/20* | (2016.01) |
| *A61B 5/283* | (2021.01) |

(Continued)

(52) U.S. Cl.
CPC .......... *A61B 34/20* (2016.02); *A61B 18/1492* (2013.01); *A61B 34/10* (2016.02);

(Continued)

(58) Field of Classification Search
CPC ... A61B 34/20; A61B 34/10; A61B 2034/102; A61B 2034/105; A61B 2034/107;

(Continued)

(56) References Cited

U.S. PATENT DOCUMENTS

| | | | | |
|---|---|---|---|---|
| 9,808,178 | B2 * | 11/2017 | Harlev | ................... A61B 5/065 |
| 2014/0024911 | A1 * | 1/2014 | Harlev | ................. A61B 5/0536 |
| | | | | 600/374 |
| 2023/0337931 | A1 * | 10/2023 | Deno | .................... A61B 5/349 |

OTHER PUBLICATIONS

Winkle et al., Physician-controlled costs: the choice of equipment used for atrial fibrillation ablation, J Interv Electrophysiol, 36: 157-165, 2013, Springer Verlag, Germany.

(Continued)

*Primary Examiner* — Eun Hwa Kim
(74) *Attorney, Agent, or Firm* — Nelson Mullins Riley & Scarborough LLP

(57) ABSTRACT

Disclosed are systems, components, devices and methods for determining locations of or imaging a catheter or other type of medical device inside a patient's body as the catheter or other type of medical device is navigated or positioned therein. In some embodiments, controlled constant current signals are transmitted through body surface electrodes into the patient's body for reception and sensing by one or more electrodes disposed on the catheter or other type of medical device as sensed electrical signals, which are then converted into sensed electrical signal values. In one embodiment, a volume of voxels is generated by one or more computing devices that corresponds to at least a portion of the patient's body where the catheter or other type of medical device is to be navigated, positioned or imaged. For at least some of the voxels, expected electrical signal values corresponding to the voxels are generated by the one or more computing devices. For corresponding given periods of time, a sequence of three-dimensional locations of the catheter or other type of medical device inside the patient's body is then determined and generated by the one or more computing devices on the basis of the sensed electrical signal values and the expected electrical signal values corresponding thereto. In another embodiment, expected signal values are not (Continued)

generated, and instead optimization problems are computed and solved to determine the three-dimensional locations of the catheter or other type of medical device inside the patient's body.

99 Claims, 19 Drawing Sheets
(11 of 19 Drawing Sheet(s) Filed in Color)

(51) Int. Cl.
   *A61B 18/14*      (2006.01)
   *A61B 34/10*      (2016.01)
   *A61B 18/00*      (2006.01)
(52) U.S. Cl.
   CPC .............. *A61B 2018/00839* (2013.01); *A61B 2034/102* (2016.02); *A61B 2034/105* (2016.02); *A61B 2034/107* (2016.02); *A61B 2034/2051* (2016.02); *A61B 2034/2055* (2016.02); *A61B 2034/2065* (2016.02)

(58) Field of Classification Search
   CPC .... A61B 2034/2051; A61B 2034/2055; A61B 2034/2065; A61B 5/283; A61B 18/1492
   See application file for complete search history.

(56)                    References Cited

OTHER PUBLICATIONS

Sirola, N., Closed-form Algorithms in Mobile Positioning: Myths and Misconceptions, 7th Workshop on Positioning, Navigation and Communication, 2010, pp. 38-44, Germany.
Jiang, N., A Large Current Source with High Accuracy and Fast Settling, Analog Dialogue 42-10, Oct. 2018, Analog Devices, USA.
Murali et al., "Cardiac Ambu. Monitoring: New Wireless Device Valid Against Conven. Holter Monitoring In a Case Series," Front. Cardiovasc. Med., Nov. 2022, Switzerland.

* cited by examiner

400

| |
|---|
| Generate a Model or Matrix of a Volume Comprising Voxels in a Patient's Body |

*401*

| |
|---|
| Generate Expected Electrical Signal Values Corresponding to Controlled Constant Current Signals Transmitted from Body Surface Electrodes Located on the Patient's Body to the Voxels |

*403*

| |
|---|
| Position and Operably Couple Body Surface Electrodes on or to the Patient's Body Surface |

*405*

| |
|---|
| Position a Medical Device or Portion Thereof Inside the Patient's Body and within the Volume |

*407*

| |
|---|
| Deliver Controlled Constant Current Electrical Signals to the Body Surface Electrodes and Transmit the Controlled Constant Current Electrical Signals into the Volume through the Electrodes |

*409*

| |
|---|
| Acquire Sensed Electrical Signals Corresponding to Received Constant Current Electrical Signals Transmitted to the Medical Device Electrodes |

*411*

| |
|---|
| Use the Sensed Constant Current Electrical Signals Values and the Expected Electrical Signal Values Corresponding Thereto to Determine Three-Dimensional Locations of the Medical Device Electrodes Inside the Patient's Body |

Comparison of Navigation Systems

| System | Accuracy | Reproducibility Precision | Map Shifts | Triangulation Errors | Hardware Complexity | Real-Time 3D Visualization | Catheter Requirements |
|---|---|---|---|---|---|---|---|
| Magnetic (Carto, Ensite, Rhythmia, Affera) | High (1-3mm) | Medium (±1mm) | Low | Medium | High (magnetic system) | Good (advanced rendering) | Specialized |
| Impedance (NavX, Acutus, CardioNXT | Medium (3-5mm) | Low (±2mm) | High | High | Medium | Good | Standard |
| Ablamap CS-Navigation | High (1 mm) | High (±1mm) | Low | None | Low | Excellent (state-of-the-art rendering) | Standard |

FIG. 23

CONTROLLED CONSTANT CURRENT SYSTEMS, DEVICES, COMPONENTS AND METHODS FOR NAVIGATING, POSITIONING, AND/OR IMAGING A MEDICAL DEVICE INSIDE A PATIENT'S BODY

FIELD OF THE INVENTION

Various embodiments described and disclosed herein relate to the field of medicine generally, and more particularly to methods, systems, devices, and components configured for navigating or determining a position, or imaging the location of, a medical device inside a patient's body.

BACKGROUND

Radiofrequency (RF) ablation is commonly employed to treat various forms of cardiac arrhythmias in patients. In some forms of cardiac arrhythmias, however, such as cardiac atrial tachycardias (AT), intra-atrial re-entry arrythmias, ventricular tachycardia, (VT), and atrial fibrillation (AF), and so on, accurate and efficacious cardiac ablation can pose a major challenge. This stems in part from the limitations of conventional fluoroscopic imaging techniques and conventional catheter-based electrophysiological (EP) mapping, and associated intra-body positioning and navigation techniques, that are used to determine the three-dimensional (3D) locations of arrhythmogenic cardiac substrates inside a patient's heart that are ablation targets.

The use of fluoroscopy for such navigation and positioning purposes can be problematic for several reasons. Fluoroscopy-guided catheter navigation is imprecise, time-consuming, and generally requires multiple different views to estimate with some degree of precision the 3D location of an ablation catheter. Moreover, using fluoroscopy, an ablation catheter often cannot be accurately and precisely returned to a previously mapped site. Fluoroscopy also exposes the patient and health care providers to radiation.

More recent and improved non-fluoroscopic mapping systems have thus been created, and have enabled physicians to overcome some of the limitations of conventional fluoroscopic mapping systems. Some of these new and improved systems can provide higher mapping resolution, 3D spatial localization, and relatively rapid acquisition of cardiac activation maps.

Examples of such new systems include the CARTO, Ensite NavX, Rythmia, Affera, Acutus, NavX and CardioNXT systems. The CARTO, Ensite NavX, Rythmia, and Affera mapping, navigation and positioning systems utilize largely magnetic-based technologies, while the Acutus, NavX and CardioNXT systems utilize primarily impedance-based technologies.

These more recent navigation, positioning and mapping systems are generally quite complicated from a technical standpoint, can require the use of expensive specialized catheters along with complex and expensive external hardware, and may be complicated or cumbersome to deploy and use. Moreover, the navigation and positioning accuracy of ablation and EP mapping catheters inside a patient's heart using some of these more recent systems can be marginal, or at least not as precise as some physicians would otherwise desire. See "Physician-controlled costs: The choice of equipment used for atrial fibrillation ablation" to Winkle et al., J Interv Card Electrophysiol (2013), 36:157-165, DOI 10.1007/s10840-013-9782-x.

What is needed are improved, less complicated, faster, more accurate, and less expensive means and methods of mapping, positioning, and navigating ablation and electrophysiological (EP) mapping catheters inside a patient's heart and other internal organs. Achieving such goals would, by way of example, enable cardiac ablation procedures to be carried out more quickly, less expensively, and with greater locational precision, and would result in higher rates of success in treating cardiac rhythm disorders such as AF.

SUMMARY

In one embodiment, there is provided a method of at least one of navigating and positioning a catheter or other type of medical device, or a portion thereof, inside a patient's body using: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough; and (d) a data acquisition or recording device operably connected to at least one computing device, the data acquisition or recording device being operably connected to the catheter electrodes and configured to acquire, or store or record, electrical signals corresponding to transmitted controlled constant current signals sensed by at least some of the plurality of catheter electrodes as sensed electrical signals, the data acquisition or recording device further being configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, or a portion thereof, inside the patient's body, where the method comprises using the at least one computing device, generating at least one three-dimensional model or matrix of a volume of a portion of the patient's body through or into which the catheter or portion thereof is to be navigated or positioned, the volume comprising a plurality of voxels, each voxel having a three-dimensional spatial coordinate within the volume; using the at least one computing device, and for each voxel or selected ones of the voxels, generating expected electrical signal values corresponding to controlled constant current signals transmitted from the body surface electrodes to each voxel or selected ones of the voxels; positioning and operably coupling the plurality of body surface electrodes on or to the first portion of the patient's body surface; positioning the catheter or a portion thereof inside the patient's body and within at least a portion of the volume; delivering, over a given period of time, the controlled constant current signals to the plurality or selected ones of the body surface electrodes for transmission into at least portions of the volume; using the data acquisition or recording device and the at least one computing device, acquiring the sensed electrical signals from the plurality or selected ones of the catheter electrodes during the given period of time, and storing or recording sensed electrical signal values corresponding to the sensed electrical signals, the sensed electrical signals corresponding to controlled constant current signals transmitted by the plurality or selected ones of the body surface electrodes into at least portions of the volume during the given period of time, and using the at least one computing device, and for at least a portion of the given period of time, determining, on the basis of the sensed electrical signal values and the expected electrical signal values corresponding thereto, at least one three-dimensional location of at least one of the catheter electrodes located within the patient's body and the at least portion of the volume during the given period of time.

Such a method may further comprise one or more of: (1) wherein following the given period of time, and during subsequent given periods of time, continuing to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and expected electrical signal values corresponding thereto, subsequent three-dimensional locations of the at least of the catheter electrodes located within the patient's body and the at least portion of the volume during each or selected ones of the subsequent given periods of time, thereby to permit navigation or positioning of the catheter or the portion thereof inside the patient's body: (2) wherein the at least one three-dimensional location of at least one of the catheter electrodes is located within the patient's heart, and further wherein the at least portion of the volume is located within the patient's heart; (3) further comprising using controlled constant current signals sensed by or transmitted from a coronary sinus catheter to compensate for at least one of movements of the patient's atria with heartbeat, movements resulting from the patient breathing, and other patient movements; (4) further comprising sensing cardiac electrical signals from the patient's heart, determining at least one shape of the patient's QRS complex from the cardiac electrical signals, and verifying or improving the accuracy of the determination of the at least one three-dimensional location; (5) further comprising, using the sensed electrical signals, reconstructing and displaying a geometry or visual model of the catheter; (6) further comprising, using the sensed electrical signals, generating an anatomical shell representation of at least a portion of an interior the patient's heart and displaying the anatomical shell representation; (7) wherein the catheter is one of a basket catheter, an electro-physiological mapping catheter, a lasso catheter, a fan-shaped catheter, an umbrella-shaped catheter, a pulsed field ablation (PFA) catheter, a coronary sinus catheter, and an ablation catheter; (8) wherein at least some of the plurality of catheter electrodes comprise one or more of sensing electrodes, ablation electrodes, electrophysiological (EP) mapping electrodes, and navigation electrodes; (9) wherein at least one corresponding ground electrode for use in conjunction with the plurality of body surface electrodes is provided; (10) wherein the at least one ground electrode is configured for placement on or over a second portion of the patient's body surface; (11) wherein the at least one controlled constant current source is configured to adjust the voltage and/or current at each body surface electrode to compensate for undesired variations in resistance or impedance at the skin-electrode interface; (12) wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape; (13) wherein the at least one controlled constant current source is at least one of an alternating current (AC) source and a direct current (DC) source; (14) wherein the at least one controlled constant current source is configured to deliver controlled constant current AC signals having frequencies ranging between about 1 kHz and about 1 MHz; (15) wherein the at least one controlled constant current source is further configured to generate and deliver controlled constant current AC signals having amplitudes ranging between about 0.1 mA and about 100 mA; (16) wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source; (17) wherein the at least one controlled constant current source is further configured to be sequentially connected to the plurality of body surface electrodes and to deliver sequentially controlled constant current signals thereto: (18) wherein the at least one controlled constant current source is further configured to be sequentially connected to each of the plurality of body surface electrodes between about once every 10 milliseconds and about once every 500 milliseconds; (19) wherein the at least one controlled constant current source is further configured to be sequentially connected to each of the plurality of body surface electrodes between about once every 100 milliseconds and once about every 300 milliseconds; (20) wherein the data acquisition or recording device further comprises amplifiers and filters configured to amplify and filter the sensed electrical signals; (21) wherein the amplifiers and filters are configured to at least one of amplify, bandpass filter, notch filter, low-pass filter, high pass filter, and digitally filter the sensed electrical signals; (22) wherein the at least one three-dimensional location of at least one of the catheter electrodes located within the patient's body and the at least portion of the volume is determined with an accuracy of about 2 mm or less; (23) wherein a number of the plurality of body surface electrodes ranges at least one of between about 2 and about 128, between about 4 and about 32, between about 1 and about 256, or between about 8 and about 64; (24) wherein the at least one three-dimensional model or matrix of the volume is generated according to at least one of the patient's body mass index (BMI), sex, weight, size, and age; (25) wherein the medical device or portion thereof is configured to be inserted into a patient's vein or artery and moved therethrough or therein; (26) wherein the medical device or portion thereof is configured to be inserted into one of a patient's coronary artery, brain, throat, esophagus, stomach, liver, urinary tract, colon, orifice, or other body organ, tissue or passageway.

In another embodiment, there is provided a system configured to navigate or position a catheter or other type of medical device, or a portion thereof, inside a patient's body, the system comprising: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough into the patient's body; and (d)

a data acquisition or recording device operably connected to at least one computing device and the catheter electrodes, and configured to acquire, or store or record, electrical signals corresponding to transmitted controlled constant current signals sensed by at least some of the plurality of catheter electrodes as sensed electrical signals, the data acquisition or recording device being further configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, or a portion thereof, inside the patient's body; wherein: (a) the at least one computing device is further configured to: (i) generate at least one three-dimensional model or matrix of a volume of a portion of the patient's body through or into which the catheter or portion thereof is to be navigated or positioned, the volume comprising a plurality of voxels, each voxel having a three-dimensional spatial coordinate within the volume; and (ii) for each voxel or selected ones of the voxels, generate expected electrical signal values corresponding to controlled constant current signals transmitted from the body surface electrodes to each voxel or selected ones of the voxels; (b) the controlled constant current source is further configured to deliver, over a given period of time, the controlled constant current signals to the plurality or selected ones of the body surface electrodes for transmission into at least portions of the volume: (c) the data acquisition or recording device and the at least one computing device are configured to acquire the sensed electrical signals from the plurality or selected ones of the catheter electrodes during the given period of time, or store or record, sensed electrical signal values corresponding to the sensed electrical signals, the sensed electrical signals corresponding to controlled constant current signals transmitted by the plurality or selected ones of the body surface electrodes into at least portions of the volume during the given period of time, and (d) the at least one computing device is configured to, for at least a portion of the given period of time, determine, on the basis of the sensed electrical signal values and the expected electrical signal values corresponding thereto, at least one three-dimensional location of at least one of the catheter electrodes located within the patient's body and the at least portion of the volume during the given period of time.

Such a system may further comprise one or more of: (1) wherein the at least one three-dimensional location of at least one of the catheter electrodes is located within the patient's heart, and further wherein the at least portion of the volume is located within the patient's heart; (2) further comprising the system being configured to use controlled constant current signals sensed by or transmitted from a coronary sinus catheter to compensate for at least one of movements of the patient's atria with heartbeat, movements resulting from the patient breathing, and other patient movements; (3) further comprising the system being configured to sense cardiac electrical signals from the patient's heart, determine at least one shape of the patient's QRS complex from the cardiac electrical signals, and verify or improve the accuracy of the determination of the at least one three-dimensional location; (4) further comprising the system being configured to use the sensed electrical signals to reconstruct and display a geometry or visual model of the catheter; (5) further comprising the system being configured to, use the sensed electrical signals, generate an anatomical shell representation of at least a portion of an interior the patient's heart, and display the anatomical shell representation; (6) wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter; (7) wherein at least some of the plurality of catheter electrodes comprise one or more of sensing electrodes, ablation electrodes, electrophysiological (EP) mapping electrodes, and navigation electrodes; (8) further comprising at least one corresponding ground electrode for use in conjunction with the plurality of body surface electrodes; (9) wherein the at least one ground electrode is configured for placement on or over a second portion of the patient's body surface; (10) wherein the at least one controlled constant current source is configured to adjust the voltage and/or current at each body surface electrode to compensate for undesired variations in resistance or impedance at the skin-electrode interface; (11) wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape; (12) wherein the at least one controlled constant current source is at least one of an alternating current (AC) source and a direct current (DC) source; (13) wherein the at least one controlled constant current source is configured to deliver constant current AC signals ranging between about 1 kHz and about 1 MHz; (14) wherein the at least one controlled constant current source is further configured to generate and deliver constant current AC signals having amplitudes ranging between about 0.1 mA and about 100 mA; (15) wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source; (16) wherein the at least one controlled constant current source is further configured to be sequentially connected to the plurality of body surface electrodes and to deliver sequentially controlled constant current signals thereto; (17) wherein the at least one controlled constant current source is further configured to be sequentially connected to each of the plurality of body surface electrodes between about once every 10 milliseconds and about once every 500 milliseconds; (18) wherein the at least one controlled constant current source is further configured to be sequentially connected to each of the plurality of body surface electrodes between about once every 100 milliseconds and once about every 300 milliseconds; (19) wherein the data acquisition or recording device further comprises amplifiers and filters configured to amplify and filter the sensed electrical signals; (20) wherein the amplifiers and filters are configured to at least one of amplify, bandpass filter, notch filter, low-pass filter, high pass filter, and digitally filter the sensed electrical signals; (21) wherein the system is further configured to permit the at least one three-dimensional location of at least one of the catheter electrodes located within the patient's body and the at least portion of the volume to be determined with an accuracy of about 2 mm or less; (22) wherein a number of the plurality of body surface electrodes ranges at least one of between about 2 and about 128, between about 4 and about 32, between about 1 and about 256, or between about 8 and about 64; (23) wherein the at least one computing device is further configured to generate the at least one three-dimensional model or matrix of the volume according to at least one of the patient's body mass index (BMI), sex, weight, size, and age; (24) wherein the catheter or portion thereof is a medical device or portion of a medical device that is configured to be inserted into a patient's vein or artery and moved therethrough or therein; and (25) wherein the medical device or portion thereof is configured to be inserted into one of a patient's coronary artery, brain, throat, esophagus, stomach, liver, urinary tract, colon, orifice, or other body organ, tissue or passageway.

In yet another embodiment, there is provided a method of at least one of navigating and positioning a catheter or other type of medical device, or a portion thereof, inside a volume of a patient's body using: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough and into the volume; and (d) a data acquisition or recording device operably connected to at least one computing device, the data acquisition or recording device being operably connected to the catheter electrodes and configured to acquire, or store or record, electrical signals corresponding to transmitted controlled constant current signals sensed by at least some of the plurality of catheter electrodes as sensed electrical signals, the data acquisition or recording device further being configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, or a portion thereof, inside the patient's body, the method comprising: positioning and operably coupling the plurality of body surface electrodes on or to the first portion of the patient's body surface; positioning the catheter or a portion thereof inside the patient's body and within at least a portion of the volume; delivering, over a given period of time, the controlled constant current signals to the plurality or selected ones of the body surface electrodes for transmission into at least portions of the volume; using the data acquisition or recording device and the at least one computing device, acquiring the sensed electrical signals from the plurality or selected ones of the catheter electrodes during the given period of time, and storing or recording sensed electrical signal values corresponding to the sensed electrical signals, the sensed electrical signals corresponding to controlled constant current signals transmitted by the plurality or selected ones of the body surface electrodes into at least portions of the volume during the given period of time, and using the at least one computing device, and for at least a portion of the given period of time, determining, on the basis of the sensed electrical signal values and computing and solving optimization problems to determine three-dimensional locations corresponding to the sensed electrical signals and their respective catheter electrodes during the given period of time, at least one three-dimensional location of at least one of the catheter electrodes located within the patient's body and the at least portion of the volume during the given period of time.

Such a method may comprise any one or more of: (1) wherein following the given period of time, and during subsequent given periods of time, continuing to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and solving optimization problems to determine the three-dimensional locations corresponding to the sensed electrical signals and their respective catheter electrodes during the subsequent given periods of time, subsequent three-dimensional locations of the at least of the catheter electrodes located within the patient's body and the at least portion of the volume during each or selected ones of the subsequent given periods of time, thereby to permit navigation or positioning of the catheter or the portion thereof inside the patient's body; (2) wherein the at least one three-dimensional location of at least one of the catheter electrodes is located within the patient's heart, and further wherein the at least portion of the volume is located within the patient's heart; (3) further comprising using controlled constant current signals sensed by or transmitted from a coronary sinus catheter to compensate for at least one of movements of the patient's atria with heartbeat, movements resulting from the patient breathing, and other patient movements; (4) further comprising sensing cardiac electrical signals from the patient's heart, determining at least one shape of the patient's QRS complex from the cardiac electrical signals, and verifying or improving the accuracy of the determination of the at least one three-dimensional location; (5) further comprising, using the sensed electrical signals, reconstructing and displaying a geometry or visual model of the catheter; (6) further comprising, using the sensed electrical signals, generating an anatomical shell representation of at least a portion of an interior the patient's heart and displaying the anatomical shell representation; (7) wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter; (8) wherein at least some of the plurality of catheter electrodes comprise one or more of sensing electrodes, ablation electrodes, electrophysiological (EP) mapping electrodes, and navigation electrodes; (9) wherein at least one corresponding ground electrode for use in conjunction with the plurality of body surface electrodes is provided; (10) wherein the at least one ground electrode is configured for placement on or over a second portion of the patient's body surface; (11) wherein the at least one controlled constant current source is configured to adjust the voltage and/or current at each body surface electrode to compensate for undesired variations in resistance or impedance at the skin-electrode interface; (12) wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape: (13) wherein the at least one controlled constant current source is at least one of an alternating current (AC) source and a direct current (DC) source; (14) wherein the at least one controlled constant current source is configured to deliver constant current AC signals ranging between about 1 kHz and about 1 MHz; (15) wherein the at least one controlled constant current source is further configured to generate and deliver constant current AC signals having amplitudes ranging between about 0.1 mA and about 100 mA; (16) wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source; (17) wherein the at least one controlled constant current source is further configured to be sequentially connected to the plurality of body surface electrodes and to deliver sequentially controlled constant current signals thereto; (18) wherein the at least one controlled constant current source is further configured to be sequentially connected to each of the plurality of body surface electrodes between about once every 10 milliseconds and about once every 500 milliseconds; (19) wherein the at least one controlled constant current source is further configured to be sequentially connected to each of the plurality of body surface electrodes between about once every 100 milliseconds and once about every 300 milliseconds; (20) wherein the data acquisition or recording device further comprises amplifiers and filters configured to amplify and filter the sensed electrical signals; (21) wherein the amplifiers and filters are configured to at least one of amplify, bandpass filter, notch filter, low-pass filter, high pass filter, and digitally filter the sensed electrical signals; (22) wherein the at least one three-dimensional location of at least one of the catheter electrodes located within the patient's body and the at least portion of the volume is determined with an accuracy of about 2 mm or less; (23) wherein a number of the plurality of body surface electrodes ranges at least one of between about 2 and about 128, between about 4 and about 32, between about 1 and about 256, or between about 8 and about 64; (24) wherein the medical device or portion thereof is configured to be inserted into a patient's vein or artery and moved therethrough or therein; and (25) wherein the medical device or portion thereof is configured to be inserted into one of a patient's coronary artery, brain, throat, esophagus, stomach, liver, urinary tract, colon, orifice, or other body organ, tissue or passageway.

In still another embodiment, there is provided a system configured to navigate or position a catheter or other type of medical device, or a portion thereof, inside a volume of a patient's body, the system comprising: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough into the patient's body and the volume; and (d) a data acquisition or recording device operably connected to at least one computing device and the catheter electrodes, and configured to acquire, or store or record, electrical signals corresponding to transmitted controlled constant current signals sensed by at least some of the plurality of catheter electrodes as sensed electrical signals, the data acquisition or recording device being further configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, or a portion thereof, inside the patient's body; wherein: (a) the controlled constant current source is configured to deliver, over a given period of time, the controlled constant current signals to the plurality or selected ones of the body surface electrodes for transmission into at least portions of the volume; (c) the data acquisition or recording device and the at least one computing device are configured to acquire the sensed electrical signals from the plurality or selected ones of the catheter electrodes during the given period of time, or store or record, sensed electrical signal values corresponding to the sensed electrical signals, the sensed electrical signals corresponding to controlled constant current signals transmitted by the plurality or selected ones of the body surface electrodes into at least portions of the volume during the given period of time, and (d) the at least one computing device is configured to, for at least a portion of the given period of time, determine, on the basis of the sensed electrical signal values and computing and solving optimization problems to determine three-dimensional locations corresponding to the sensed electrical signals and their respective catheter electrodes during the given period of time, at least one three-dimensional location of at least one of the catheter electrodes located within the patient's body and the at least portion of the volume during the given period of time.

Such a system may further comprise any one or more of: (1) wherein following the given period of time, and during subsequent given periods of time, the system is configured to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and solving optimization problems to determine the three-dimensional locations corresponding to the sensed electrical signals and their respective catheter electrodes during the subsequent given periods of time, subsequent three-dimensional locations of the at least one of the catheter electrodes located within the patient's body and the at least portion of the volume during each or selected ones of the subsequent given periods of time, thereby to permit navigation or positioning of the catheter or the portion thereof inside the patient's body: (2) wherein the at least one three-dimensional location of at least one of the catheter electrodes is located within the patient's heart, and further wherein the at least portion of the volume is located within the patient's heart; (3) further comprising using controlled constant current signals sensed by or transmitted from a coronary sinus catheter to compensate for at least one of movements of the patient's atria with heartbeat, movements resulting from the patient breathing, and other patient movements; (4) further comprising sensing cardiac electrical signals from the patient's heart, determining at least one shape of the patient's QRS complex from the cardiac electrical signals, and verifying or improving the accuracy of the determination of the at least one three-dimensional location; (5) further comprising, using the sensed electrical signals, reconstructing and displaying a geometry or visual model of the catheter; (6) further comprising, using the sensed electrical signals, generating an anatomical shell representation of at least a portion of an interior the patient's heart and displaying the anatomical shell representation; (7) wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter; (8) wherein at least some of the plurality of catheter electrodes comprise one or more of sensing electrodes, ablation electrodes, electrophysiological (EP) mapping electrodes, and navigation electrodes; (9) wherein at least one corresponding ground electrode for use in conjunction with the plurality of body surface electrodes is provided; (10) wherein the at least one ground electrode is configured for placement on or over a second portion of the patient's body surface; (11) wherein the at least one controlled constant current source is configured to adjust the voltage and/or current at each body surface electrode to compensate for undesired variations in resistance or impedance at the skin-electrode interface; (12) wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape; (13) wherein the at least one controlled constant current source is at least one of an alternating current (AC) source and a direct current (DC) source; (14) wherein the at least one controlled constant current source is configured to deliver constant current AC signals ranging between about 1 kHz and about 1 MHz; (15) wherein the at least one controlled constant current source is further configured to generate and deliver constant current AC signals having amplitudes ranging between about 0.1 mA and about 100 mA; (16) wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source; (17) wherein the at least one controlled constant current source is further configured to be sequentially connected to the plurality of body surface electrodes and to deliver sequentially controlled constant current signals thereto; (18) wherein the at least one controlled constant current source is further configured to be sequentially connected to each of the plurality of body surface electrodes between about once every 10 milliseconds and about once every 500 milliseconds; (19) wherein the at least one controlled constant current source is further configured to be sequentially connected to each of the plurality of body surface electrodes between about once every 100 milliseconds and once about every 300 milliseconds; (20) wherein the data acquisition or recording device further comprises amplifiers and filters configured to amplify and filter the sensed electrical signals; (21) wherein the amplifiers and filters are configured to at least one of amplify, bandpass filter, notch filter, low-pass filter, high pass filter, and digitally filter the sensed electrical signals; (22) wherein the at least one three-dimensional location of at least one of the catheter electrodes located within the patient's body and the at least portion of the volume is determined with an accuracy of about 2 mm or less; (23) wherein a number of the plurality of body surface electrodes ranges at least one of between about 2 and about 128, between about 4 and about 32, between about 1 and about 256, or between about 8 and about 64; (24) wherein the medical device or portion thereof is configured to be inserted into a patient's vein or artery and moved therethrough or therein; and (25) wherein the medical device or portion thereof is configured to be inserted into one of a patient's coronary artery, brain, throat, esophagus, stomach, liver, urinary tract, colon, orifice, or other body organ, tissue or passageway.

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

FIG. 4 shows a flow diagram corresponding to one embodiment of a method of navigating, positioning, and/or imaging a medical device or catheter 110 inside a human body;

FIG. 23 shows a table comparing some of the characteristics of the controlled constant current medical device navigation, positioning and/or imaging system described and disclosed herein to those of several different commercially available medical device navigation systems.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for one or more of EP mapping, and/or navigating or determining a position of a medical device such as an ablation and/or EP mapping catheter, or imaging the medical device, inside a patient's body (e.g., inside the patient's heart, stomach, brain or other internal organ, passageway, or other internal portion of the body).

Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Various embodiments of electrographic flow (EGF) techniques, methods, systems, devices, and components may be employed efficaciously in conjunction with the controlled constant current navigation, positioning and imaging systems, devices, components and methods disclosed and described herein.

Figure 1:
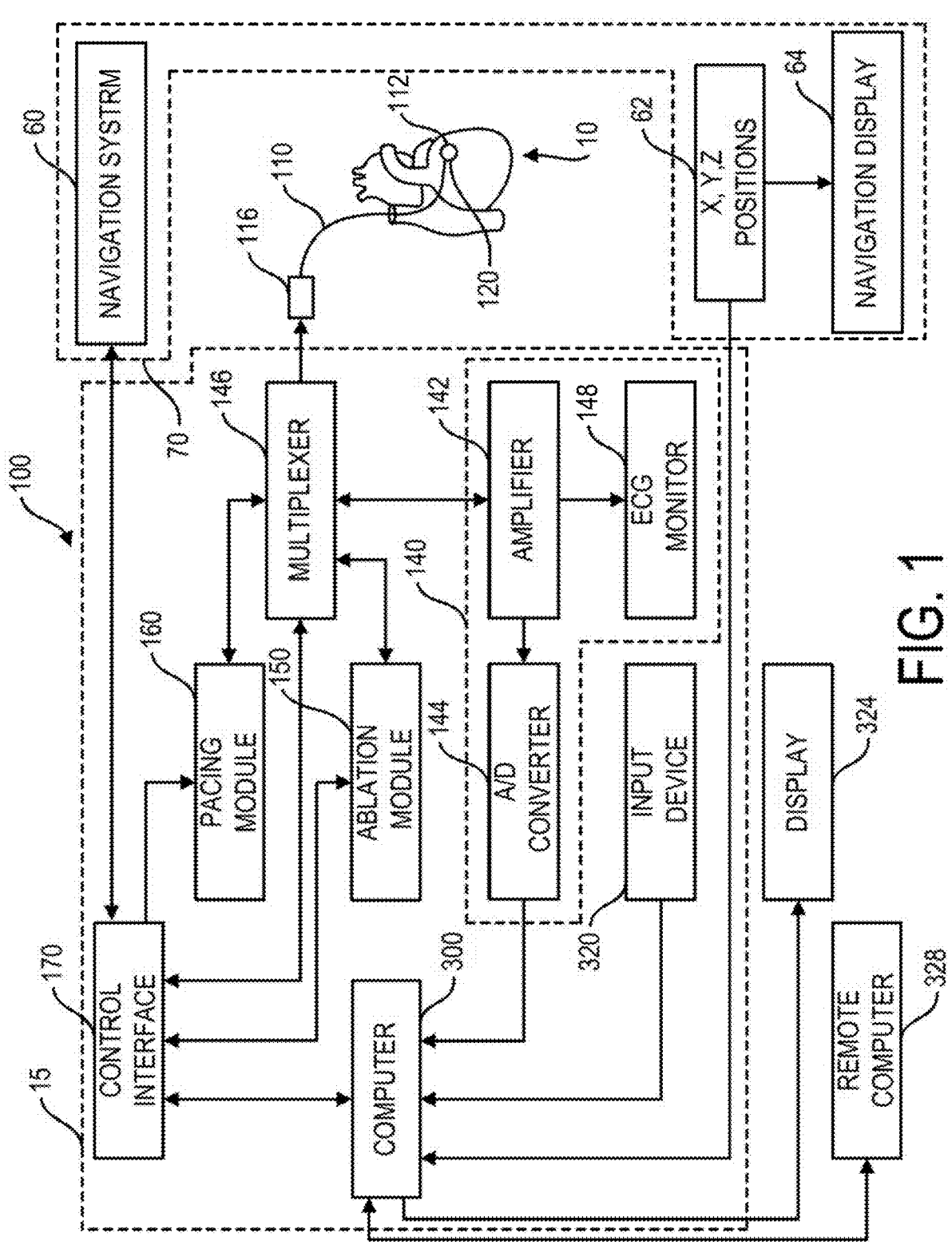
FIG. 1 shows one embodiment of a combined cardiac electrophysiological mapping (EP), pacing and ablation system 100.

Referring now to FIG. 1, there is illustrated one embodiment of a combined cardiac electrophysiological mapping (EP), pacing and ablation system 100. Note that in some embodiments system 100 may not include ablation module 150, pacing module 160, and/or multiplexer 146. Among other things, the embodiment of system 100 shown in FIG. 1 is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1 comprises five main functional units: electrophysiological mapping (EP mapping unit) 140 (which is also referred to herein as data acquisition device 140), multiplexer 146, ablation module 150, pacing module 160, imaging and/or navigation system 70, and computer or computing device 300. Data acquisition, processing and control system 15 comprises data acquisition device 140, multiplexer 146, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 146, 150, 160, 170 and 70 may be controlled separately by each of such systems, modules and devices, or by some combination of such systems, modules and devices.

Instead of being operably connected (e.g., through Bluetooth signals, a LAN or WAN network, or through the cloud), or directly connected, to computing device 300, data acquisition device 140 may be configured to provide as outputs therefrom saved or stored body surface electrogram signals, which can be, by way of example, saved or stored on a hard drive, in a memory, in the cloud, remotely, on a USB stick, or other suitable storage device, and where the saved or stored body surface electrogram signals are later or subsequently provided as inputs to computing device 300 for processing and analysis.

Computer or computing device 300 may be configured to receive operator inputs from an input device 320 such as a keyboard, mouse and/or control panel, ore remotely. Outputs from computer 300 may be displayed on display or monitor 324 or other output devices (not shown in FIG. 1). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, pulsed field ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional body surface electrodes may also serve as detectors of surface ECGs. In one embodiment, the analog signals obtained from the intracardiac and/or body surface electrodes may be routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 is a basket catheter that includes a plurality of 64 electrodes, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes in catheter 110 are, however, also contemplated. In most of the various embodiments, at least some electrodes, probes and/ or sensors included in catheter 110 are configured to detect cardiac activation or electrical signals to generate electrocardiograms or electrogram signals, and/or to detect constant current electrical signals transmitted from body surface electrodes into the patient's heart (more about which is said below). These signals are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140. In still further embodiments, multiplexer 146 is optional or not provided at all, and data acquisition device 140, ablation module 150, and/or pacing module 160 are employed separately and/or operate independently from one another. In addition, in some embodiments computing device 300 may be combined or integrated with one or more of data acquisition device 140, ablation module 150, and/or pacing module 160.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

Figure 3:
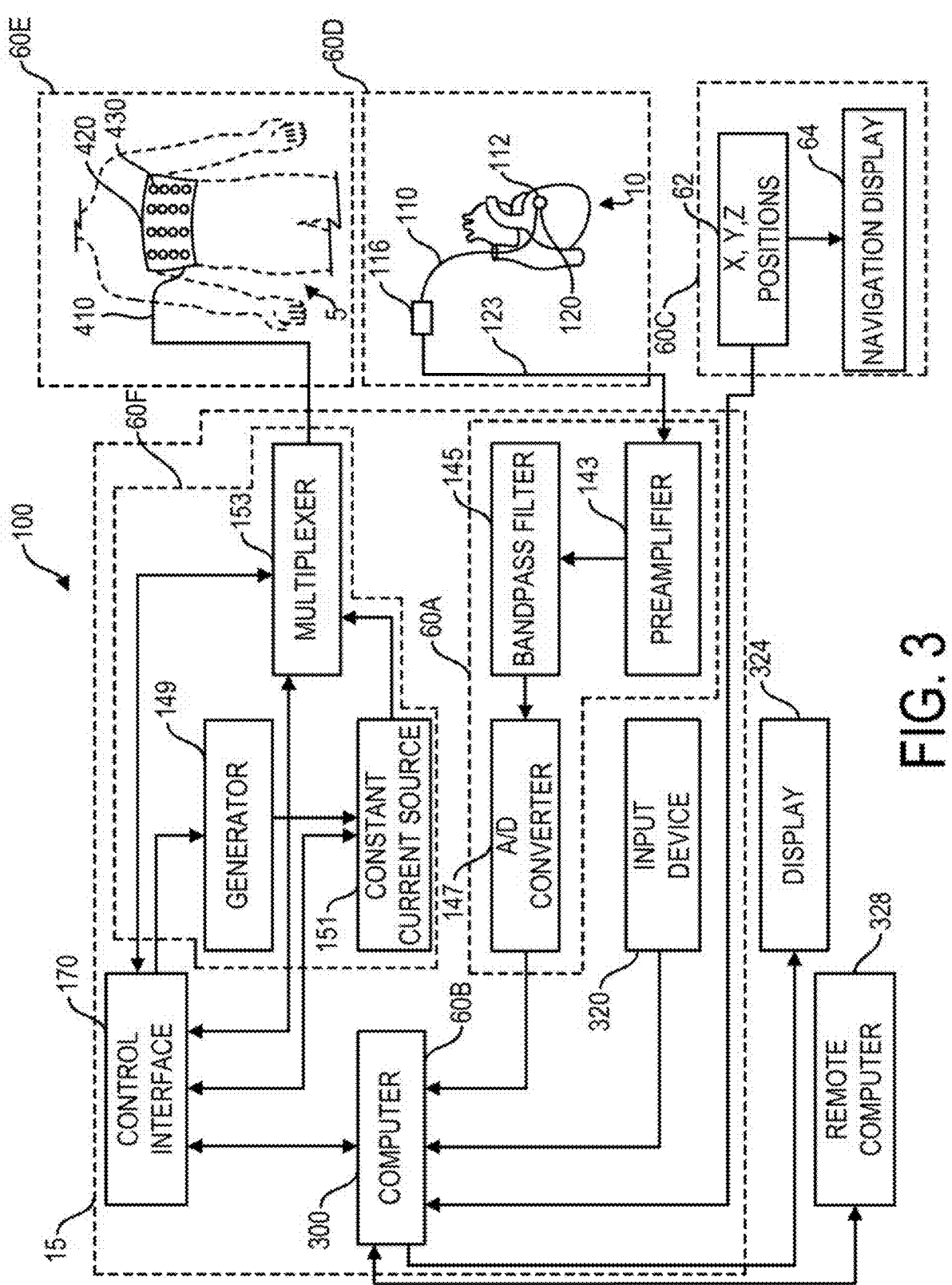
FIG. 3 shows one embodiment of a medical device or catheter controlled constant current navigation, positioning and/or imaging system 100.

In another embodiment, or in an enhanced or supplemented embodiment, a medical practitioner or health care professional also employs catheter 110 as a roving catheter to locate the site of the location of the source of a cardiac rhythm disorder or irregularity in the endocardium quickly and accurately, where navigation, and positioning of catheter 110 inside the patient's heart is accomplished using the controlled constant current techniques described and disclosed in further detail below (see, for example, FIG. 3).

In one embodiment, the electrogram signal data and/or controlled constant current signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10, and/or of the electrodes located at or near the distal end of catheter 110. This permits a medical practitioner to move interactively and quickly the electrodes of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magneto-cardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1, EP mapping system or data acquisition device 140 may be configured to condition the analog electrogram signals or controlled constant current signals received and delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1, and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1B). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1B). One embodiment of an ablation method and device is disclosed in U.S. Pat. No. 5,383,917 to Desai et al.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1B). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

In one embodiment, computing device or computer 300 may be appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1, system 100 also comprises a physical imaging and/or navigation or positioning system 70, which may or may not employ the controlled constant current mapping, imaging, navigation, and/or positioning techniques described below. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, an electrical impedance tomography EIT) system, a controlled constant current system (as described below), or any one or more of the CARTO, Ensite NavX, Rythmia, Affera, Acutus, NavX and CardioNXT systems. Operation of system 70 be controlled by computer 300 via control interface 170, or by other control means incorporated into or operably connected to imaging or navigation or positioning system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 60 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70. Alternatively, and as further described below, controlled constant current signals received by sensing or receiving electrodes included in mapping electrode assembly 120 or otherwise located on catheter 110 may be used to navigate or position catheter 110, or to provide images of the locations of such electrodes or portions of catheter 110.

Medical navigation systems suitable or adaptable for use in conjunction with the various embodiments described and disclosed herein include, but are not limited to, image-based navigation systems, model-based navigation systems, optical navigation systems, electromagnetic navigation systems (e.g., BIOSENSE® WEBSTER® CARTO® system), impedance-based navigation systems (e.g., the St. Jude® ENSITE™ VELOCITY™ cardiac mapping system), systems that combine attributes from different types of imaging and navigation systems and devices to provide navigation within the human body (e.g., the MEDTRONIC®) STEALTHSTATION® system), and various embodiments of the controlled constant current navigation, positioning and/or imaging system described in detail below.

In view of the structural and functional descriptions provided herein, those skilled in the art will appreciate that portions of the described devices and methods may be configured as processes, methods, data processing systems, and/or computer methods. Accordingly, these portions of the devices and methods described herein may take the form of a hardware embodiment, a software embodiment, or an embodiment combining software and hardware, such as shown and described with respect to computer system 300 illustrated in FIG. 2.

Furthermore, portions of the devices and methods described herein may be a process or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, processes, and systems. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 2:
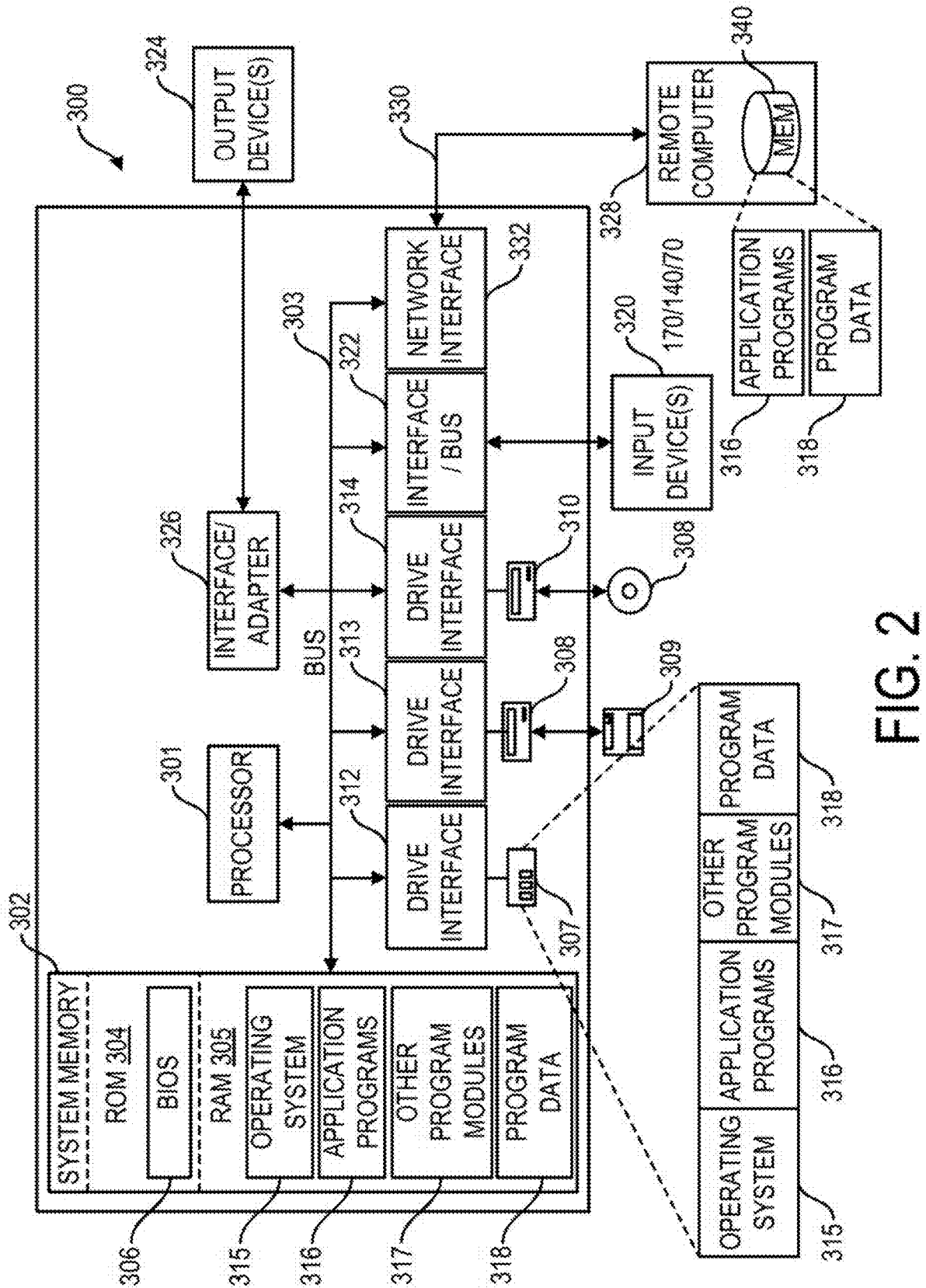
FIG. 2 shows one embodiment of a computer system 300.

In this regard, FIG. 2 illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, to process received controlled constant current constant electrical signals, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/ nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein.

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Referring now to FIG. 3, there are shown and illustrated various aspects of one embodiment of a controlled constant current navigation or positioning, and optionally imaging, system 60, which in the illustrated embodiment comprises principal components: (a) received constant current signal conditioning and conversion module 60A; (b) computer 60B/300; (c) navigation, position and/or image display module 60C; (d) constant current signal receiving catheter 60D; (e) body surface electrode system 60E, and (f) controlled constant current system 60F. Note that one or more of the various systems, modules, components and devices illustrated in FIG. 3 may be combined with, added to, or operate in conjunction with those illustrated in FIGS. 1 and 2.

In FIG. 3, there is shown a patient 5 wearing a body surface electrode vest 420 comprising a plurality of body surface electrodes 430, which are operably connected to module 60F through electrical connection 410. (Wireless connections may also be employed to replace electrical connection 410.) A high frequency RF generator 149 generates signals that are provided to high-fidelity controlled constant current source 151, which is configured to emit selectable current signals having a degree of accuracy and repeatability. The controlled constant current signals output from constant current source 151 are next provided to multiplexer 153, and thence to medical device/catheter connection 410 and body surface electrodes 430.

Note that electrode vest 420 may be replaced by one or a plurality of electrode strips comprising electrodes 430, by individual electrodes 430 attached or coupled directly to patient 5's body or torso, or any combination thereof. Body surface electrodes 430 are positioned on patient 5's body such that they overlie a volume of interest in patient 5, which in the embodiment illustrated in FIG. 3 includes the patient's heart 10.

Body surface electrodes 430 and module 60F of system 100 are configured to deliver individual, high-fidelity, controlled, constant current, electrical signals to the volume of interest located beneath electrodes 430. In one embodiment, each electrode 430 transmits into the volume or region of interest a controlled constant current signal which is different in phase, amplitude and/or frequency from the controlled constant current signals transmitted by other electrodes 430.

In another embodiment, electrodes 430 may be configured to emit controlled constant current electrical signals that have the same or similar phases, amplitudes and/or frequencies, but which owing to their different locations on the surface of the patient's body, and the different portions of body 5 such signals traverse on their way to sensing or receiving electrodes located within the volume, can result in such signals having different distinguishable characteristics (including, but not limited to, variations in amplitude or phase) when they arrive at the various sensing or reception electrodes located within the volume and patient's body 5.

In yet another embodiment, instead of a "scan" of controlled constant current signals of the same or similar waveform characteristics being transmitted across and through body surface electrodes 430, each body surface electrode 430 transmits a controlled constant current signal having its own unique AC frequency. Such unique AC frequency signals can then be detected by electrodes located on medical device or catheter 110, and using appropriate analog signal bandpass or other digital filtering techniques be differentiated from one another to yield 3D electrode positions.

Thus, and in such embodiments, each body surface electrode 430 transmits a controlled constant current signal that is received by each sensing electrode within the volume as a unique controlled constant current signal owing to, for example, phase, frequency and/or amplitude differences. Together, and with further reference to FIGS. 10 and 14, it will be seen that at each receiving or sensing electrode of medical device or catheter 110 located within the volume, a collective pattern of voltages received by the receiving or sensing electrodes results. In conjunction with one another, the controlled constant current signals transmitted by electrodes 430 and received by the sensing or receiving electrodes of medical device or catheter 110 together permit the X,Y,Z or 3D locations or positions of electrodes located on catheter or medical device 110 and within the volume to be determined, more about which is said below.

Module 60A of system 100 is configured to receive and process the controlled constant current electrical signals transmitted by electrodes 430 and sensed or received by electrodes located on medical device or catheter 110. Such received or sensed controlled constant current electrical signals are routed from medical device or catheter 110 through electrical connection 123 to module 60A. (Wireless connections may also be employed to replace electrical connection 123.) Preamplifier 143 is amplify configured to receive the controlled constant current signals sensed or received thereby, and to condition and convert such signals for further processing by bandpass filter 145. In some embodiments, electrical connection or cable 123 or 410 can be replaced by a wireless connections, such as BLUETOOTH® connection. In one embodiment, and as shown in FIG. 3, constant current signals received by sensing electrodes located on catheter or medical device 110 are directed first to preamplifier 143, then to bandpass filter 145, and last to A/D converter 147 before being received by computer 300 for further processing and analysis. Note that sensing or receiving electrodes located on medical device 110 may also be configured to perform other functions, such as to act as fiducial markers, ablation electrodes, pacing electrodes, defibrillation electrodes, and so on.

In FIG. 3, and in one embodiment, 16 body surface electrodes 430 are mounted on, attached to, or operably coupled to patient 5's thorax or body above the volume (or region of interest). In one embodiment, a corresponding ground electrode pad or one or more ground electrodes are optimally placed diametrically opposite transmitting electrodes 430 on the patient back. Other numbers and configurations of body surface and ground electrodes are also contemplated. As regards ground electrodes, many options exist, including no explicitly provided ground electrode (a ground will nearly always be found for a transmitted electrical signal), substitutes for specific or discrete ground electrodes such as a metal or electrically conductive bed or surgery platforms, pans, leashes, collars, and so on.

As regards transmitting electrodes, the number of such electrodes employed may range, by way of non-limiting example, between 1 electrode and 3 electrodes, 4 electrodes, 8 electrodes, 12 electrodes, 16 electrodes, 24 electrodes, 36 electrodes, 48 electrodes, 64 electrodes, 72 electrodes, 96 electrodes, 128 electrodes, 256 electrodes, 512 electrodes, and 1,024 electrodes, and so on.

Some examples of current manufacturers of cardiac monitoring patches, which in at least some cases may be adapted or configured for use as electrode patches configured to transmit or deliver controlled constant current signals, include: (a) iRhythm® and their Zio XT® and Zio T® Patch product offerings; or (b) the Bardy Dx® Carnation Ambulatory Monitor (CAM™). Electrodes configured to operate wirelessly, such as those found in the NUVANT® Mobile Cardiac Telemetry (MCT) Monitor, which communicates wirelessly with a cellular device, are also contemplated.

See, for example: (1) U.S. Pat. No. 10,123,703 entitled "Health monitoring apparatus with wireless capabilities for initiating a patient treatment with the aid of a digital computer" to Bardy et al. ("the '703 patent"): (2) U.S. Pat. No. 10,299,691 entitled "Wearable monitor with arrhythmia burden evaluation" to Hughes et al. ("the '691 patent"); (3) U.S. Pat. No. 10,772,522 entitled "Disposable biometric patch device" to Zadig, and (4) "Cardiac Ambulatory Monitoring: New Wireless Device Validated Against Conventional Holter Monitoring in a Case Series" to Murali et al., Front. Cardiovasc. Med., 30 Nov. 2020 (https://doi.org/10.3389/fcvm.2020.587945) describing the SmartCardia® wearable cardiac monitoring patch ("the Murali paper"). Those skilled in the art will realize that certain aspects and features disclosed and described in in the '703 patent, the '691 patent, the '522 patent, and the Murali paper can be employed in, or adapted and modified for use in, the systems, devices, components, and methods described and disclosed herein. The '703 patent, the '691 patent, the '522 patent, and the Murali paper incorporated by reference herein, each in its respective entirety. Apple iWatch®, FitBit®, Galaxy Watch3®, and Galaxy Watch Active2® are examples of watch or watch-like devices configured to acquire cardiac data from the wearer, such as ECGs, blood pressure, heart rate, etc., Such wearable devices likewise contain certain aspects and features that can be employed in, or adapted and modified for use in, the systems, devices, components, and methods described and disclosed herein.

In the example of FIG. 3, there are shown 16 body surface electrodes 430 mounted on the anterior portion of vest 420, which in turn is worn on or attached to the thorax of patient 5. In some embodiments, by way of non-limiting example, another 16 body surface electrodes 430 may be mounted on a posterior surface of vest 420 (not shown in FIG. 3).

It is further contemplated that body surface electrodes 430 may be mounted, attached or coupled to the patient's thorax by means other than a vest, such as by patches, electrode strips, individually, or by other means known in the art. For example, electrode strips manufactured by Goltec GmbH of Cremlingen, Germany can be used. Carbon and metal body surface electrode strips are available from Goltec GmbH. Carbon electrode strips have the advantage of being radiotranslucent, i.e., being transparent or substantially transparent during X-ray imaging.

Electrodes may be provided only on the anterior portion of the patient's thorax, only on the posterior portion of the patient's thorax, on side or lateral portions of the patient's thorax, or on any suitable combination of anterior, posterior and/or lateral portions of the patient's thorax.

In applications where the region of interest or volume is not patient 5's heart, transmitting electrodes 430 can be positioned above or below the volume, where the region of interest includes, by way of non-limiting example, patient 5's brain, stomach, kidneys, bladder, colon, large intestine, small intestine, and/or any other internal organ, passageway, or the like which is to be investigated and analyzed using, for example, a catheter or other device configured to be placed inside the human body.

Continuing to refer to FIG. 3, and as mentioned above, in one embodiment electrodes 430 are configured to transmit controlled constant current electrical signals in the direction of or into a volume containing or encompassing patient's heart 10. In addition to transmitting electrodes 430, other types of devices and/or transducers, such as ground electrodes, navigation patches, position markers, or other devices may be configured to operate in conjunction with, be incorporated into, or form a portion of vest 420, electrodes 430, and/or system 100. Electrodes 430 may be reusable or disposable, unipolar or bipolar, and may be configured for use with MRT/MRI, X-Ray, and/or CAT scanning imaging systems or other types of imaging systems 60. Imaging and/or navigation system 60 may also be employed used to help identify and determine the precise positions of the various electrodes 430 or position markers included in vest 430. Gels, adhesives, and liquids may be employed to improve electrical coupling of electrodes 430 with the patient's body, as is well known in the art.

In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60.

Note that in some embodiments, and as described in some detail above, system 100 of FIGS. 1 and 3 may not include multiplexer 146, ablation module 150, pacing module 160, imaging and/or navigation system 60, or other modules or components shown in FIGS. 1 and 3. Among other things, the embodiments of system 100 shown in FIGS. 1 and 3 may be configured to detect and reconstruct cardiac activation information acquired from a patient's heart relating to cardiac rhythm disorders and/or irregularities, and may further be configured to detect and discover the locations of the source of such cardiac rhythm disorders and/or irregularities with enhanced precision relative to prior art techniques using body surface electrodes 430. In some embodiments, system 100 is further configured to treat the location of the source of the cardiac rhythm disorder or irregularity, for example by ablating the patient's heart at the detected source location.

The embodiment of system 100 shown in FIGS. 1 and 3 may include at least one computer or computing device or system 300 employed to control the operation of one or more of systems, modules and/or devices included in 60, 70, 100, 140, 150, 160, and 170. Alternatively, the respective operations of systems, modules or devices 60, 70, 100, 140, 150, 160, and 170 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIGS. 1 and 3). Computer 300 may also be operably connected to a remote computer or analytic database or server 328. At least each of components, devices, modules and systems 60, 70, 100, 110, 140, 146, 148, 150, 170, 300, 324, 328, 410, 420, and 430 may be operably connected to other components or devices by wireless (e.g., BLUETOOTH) or wired means. Data may be transferred between components, devices, modules or systems through hardwiring, by wireless means, or by using portable memory devices such as USB memory sticks.

During navigation, positioning, imaging, body surface EP mapping, and/or EGF analysis procedures, and as described above, body surface electrodes 430 are positioned on the thorax of patient 5, and by way of example may be mounted on a vest 420 that is configured to place individual electrodes 430 in predetermined positions on the patient's body. These predetermined electrode positions can also be provided to imaging and/or positioning or navigation system 60 and/or to computer 300 as a data file so that the spatial positions of body surface electrodes 430 are known (at least approximately), and so that EGF and/or navigation/positioning/imaging analysis can be carried out as described and disclosed herein.

When system 100 of FIGS. 1 and 3 is operating in an EP mapping or EGF mode, body surface electrodes 430, or other body surface electrodes, may also function as detectors of electrocardiographic signals. In one embodiment, the analog signals obtained from body surface electrodes 430 can be routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals may also be digitized via ADC 144 and input into computer 300 for data processing. EGF analysis and graphical display.

In one embodiment, controlled constant current medical device navigation, positioning and imaging technology employs an approximately two-dimensional scanning method, where a controlled constant current source is located over the chest of patient 5 where heart 10 is located. As described above, and in one embodiment, scanning is performed using a matrix or array of skin or body surface electrodes 430 driven by a multiplexer 153, and applying a spherically divergent field of electrical current in the long wave RF range of frequency. By reading the induced voltage pattern at locations within the volume or matrix using catheter receiving or sensing electrodes, and reconstructing a 3D matrix from the induced voltage pattern, the exact positions of the catheter receiving electrodes within the body and the volume can be determined with a great deal of locational precision.

By applying the current generated by controlled constant current sources located at the patient's body surface, the voltage profile created by the current within the heart chambers and the volume is independent from the access resistances of individual electrodes 430. The matrix of electrodes 430 of known spacing D1 and D2 allows the controlled constant current scan to directly provide absolute rectangular coordinates.

To compensate for movements of the atria with heartbeat, breathing, and patient movements, in one embodiment a coronary sinus (CS) or other catheter can be used as a reference. As a second reference system, the local shape of a QRS complex in an electrogram, which differs depending on a catheter electrode's location, can be mapped to 3D space using, for example, a neural network where the QRS shapes detected at each CS electrode on a CS catheter are monitored in real time or near-real-time, and shifts in position of the catheter are detected by determining whether the shapes of the QRS complexes exceed a predetermined threshold or other pertinent parameter. See: (a) U.S. patent application Ser. No. 17/831,249 to Tenbrink et al. entitled "Methods, Systems, Devices, and Components for Extracting Atrial Signals from QRS and QRST Complexes" filed on Jun. 2, 2022 (hereafter "the '249 patent application); (b) U.S. patent application Ser. No. 17/863,246 to Denner et al. entitled "Biosignal-Based Intracardiac Navigation Systems, Devices, Components and Methods" filed on Jul. 12, 2022 (hereafter "the '246 patent application); and (c) U.S. patent application Ser. No. 18/125,630 to Grund et al. entitled "Systems, Devices, Components and Methods for Electroanatomical Mapping of the Heart Using 3D Reconstructions Derived from Biosignals" filed on Mar. 23, 2023 (hereafter "the '630 patent application). The '249, '246, and '630 patent applications are incorporated by reference herein, each in its respective entirety.

Referring now to FIGS. 4-23, overall controlled constant current technology will be seen to offer a unique approach to navigation, positioning and imaging that provides accurate, high-resolution imaging of the heart or a medical device without being affected by electrode access or input resistances or impedances, or patient movements.

FIG. 4 illustrates one method of employing some of the embodiments of the controlled constant current navigation, positioning and/or imaging systems described and disclosed herein. In method 400 of FIG. 4, at step 401 a model of a volume, or region or volume of interest, comprising voxels is generated for the patient's body. In some embodiments, the model or volume is specifically generated to include and focus upon patient's heart 10, and may incorporate details regarding a specific patient's age, size, sex, body mass index (BMI), fatness, leanness, or thickness of tissue, musculature, bone characteristics, and/or cardiac characteristics (e.g., cardiomyopathy, etc.). At step 402, electrical signal values corresponding to controlled constant current signals transmitted from body surface electrodes 430 located on the patient's body 5 to the voxels in the volume are generated. At step 405, body surface electrodes 430 are positioned and operably coupled on or to patient's 5's body surface. At step 407, a medical device or portion thereof (such as a catheter) is positioned inside the patient's body and within the volume, where the medical device comprises receiving or sensing electrodes configured to receive controlled constant current signals transmitted by body surface electrodes 430. At step 409, controlled constant current electrical signals are delivered to body surface electrodes 430 and transmitted into the volume or region of interest through electrodes 430. At step 411, electrical signals corresponding to constant current electrical signals transmitted to and received by sensing electrodes mounted on near the medical device are acquired by the sensing ort receiving electrodes located on the medical device. At step 413, the sensed constant current electrical signals values and the expected electrical signal values corresponding thereto are employed to determine the three-dimensional locations of the medical device sensing or receiving electrodes located inside the patient 5's body and within the volume or region of interest. The expected electrical signal values are generated using the known predetermined amplitudes, phases, and/or frequencies of the unique transmitted controlled constant current signals generated, or that are to be generated, by constant current source 151 and transmitted into the volume or region of interest by electrodes 430 for reception or sensing by electrodes located on medical device or catheter 110.

In respect of foregoing steps 410 through 413, further aspects of such steps may include, but are not limited to, one or more of the following: (a) body surface electrodes 430 being configured for placement on or over a first portion of the patient 5's body surface; (b) a plurality of receiving or sensing electrodes mounted on or attached to the catheter or medical device 110, each such electrode having a predetermined location or position on or in the catheter or medical device; (c) at least one controlled constant current source 151 configured to be operably connected to the plurality or selected ones of the body surface electrodes 430 and to transmit controlled constant current signals therethrough; (d) a data acquisition or recording device 60A operably connected to at least one computing device 60B/300, the data acquisition or recording device 60A being operably connected to the catheter or medical device electrodes and configured to acquire, or store or record, electrical signals corresponding to transmitted controlled constant current signals sensed by at least some of the plurality of catheter electrodes as sensed electrical signals; (e) the data acquisition or recording device 60A further being configured to relay sensed electrical signals to computing device 60B/300 as sensed electrical signal values, the at least one computing device 60B/300 comprising at least one non-transitory computer readable medium configured to store instructions executable by at least one processor to permit navigation or positioning of the catheter or other type of medical device 110, or a portion thereof, inside the patient 5's body; (e) using the at least one computing device 60B/300, generating at least one three-dimensional model or matrix of a volume of a portion of the patient's body through or into which catheter or medical device 100 (or a portion thereof) is to be navigated or positioned, the volume comprising a plurality of voxels, each voxel having a three-dimensional (3D) spatial coordinate within the volume; (f) using the at least one computing device 60B/300, and for each voxel or selected ones of the voxels, generating expected electrical signal values corresponding to controlled constant current signals transmitted from body surface electrodes 430 to each voxel or selected ones of the voxels; (g) positioning and operably coupling the plurality of body surface electrodes 430 on or to the first portion of the patient's body surface; (h) positioning the catheter or medical device 110, or a portion thereof, inside the patient's body and within at least a portion of the volume; (h) delivering, over a given period of time, the controlled constant current signals to the plurality or selected ones of the body surface electrodes 430 for transmission into at least portions of the volume; (i) using the data acquisition or recording device 60A and the at least one computing device 60B/300, acquiring the sensed electrical signals from the plurality or selected ones of the catheter or medical device electrodes 430 during the given period of time, and storing or recording the sensed electrical signal values corresponding to the sensed electrical signals, the sensed electrical signals corresponding to controlled constant current signals transmitted by the plurality or selected ones of the body surface electrodes 430 into at least portions of the volume during the given period of time; (j) using the at least one computing device 60B/300, and for at least a portion of the given period of time, determining, on the basis of the sensed electrical signal values and the expected electrical signal values corresponding thereto, at least one three-dimensional location of at least one of the catheter or medical device electrodes located within the patient's body and the at least portion of the volume during the given period of time.

Still further aspects of employing some of the embodiments of the controlled constant current navigation, positioning and/or imaging systems described and disclosed herein include, but are not limited to, the following: (a) following the given period of time, and during subsequent given periods of time, continuing to: (i) transmit controlled constant current signals through the body surface electrodes 430 into patient's body 5 and the at least portion of the volume; (b) acquire sensed electrical signals; (c) store or record sensed electrical signal values, and (d) determine, on the basis of the sensed electrical signal values and expected electrical signal values corresponding thereto, subsequent three-dimensional locations of the catheter or medical device electrodes located within patient's body 5 and the at least portion of the volume during each or selected ones of the subsequent given periods of time, thereby to permit navigation, positioning and/or imaging of the catheter or medical device 100, or portion thereof, inside patient's body 5.

Yet further aspects of employing some of the embodiments of the controlled constant current navigation, positioning and/or imaging systems described and disclosed herein include, but are not limited to, the following: (a) the at least one three-dimensional location of at least one of the catheter or medical device electrodes is located within patient's heart 10, and further wherein the at least portion of the volume is located within the patient's heart; (b) using controlled constant current signals sensed by or transmitted from a coronary sinus catheter to compensate for at least one of movements of the patient's atria with heartbeat, movements resulting from the patient breathing, and other patient movements; (c) sensing cardiac electrical signals from the patient's heart, determining at least one shape of the patient's QRS complex from the cardiac electrical signals, and verifying or improving the accuracy of the determination of the at least one three-dimensional location provided by the controlled constant current navigation, positioning or imaging system 100; (d) using the sensed electrical signals, reconstructing and displaying a geometry or visual model of the catheter or medical device 110; (e) using the sensed electrical signals, generating an anatomical shell representation of at least a portion of an interior the patient's heart 10 and displaying the anatomical shell representation on display 64; (f) wherein the catheter 110 is one or more of a basket catheter, an electrophysiological mapping catheter, a lasso catheter, a fan-shaped catheter, an umbrella-shaped catheter, a pulsed field ablation (PFA) catheter, a coronary sinus catheter, or an ablation catheter; (g) wherein at least some of the plurality of catheter electrodes comprise one or more of sensing electrodes, ablation electrodes, electro-physiological (EP) mapping electrodes, and navigation electrodes; (h) wherein at least one corresponding ground electrode for use in conjunction with the plurality of body surface electrodes 430 is provided; (i) wherein at least one ground electrode is configured for placement on or over a second portion of the patient's body surface; (j) wherein the plurality of body surface electrodes 430 are configured in an array; (k) wherein the body surface electrode array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape; (l) wherein the at least one controlled constant current source 151 is at least one of an alternating current (AC) source and a direct current (DC) source; (m) wherein the at least one controlled constant current source 151 is configured to deliver constant current AC signals ranging between about 1 kHz and about 1 MHz in frequency; (n) wherein the at least one controlled constant current source is further configured to generate and deliver constant current AC signals having amplitudes ranging between about 0.1 mA and about 100 mA; (o) wherein the at least one controlled constant current source is further configured to be sequentially connected to the plurality of body surface electrodes 430 and to deliver sequentially controlled constant current signals thereto, for example through multiplexer 153; (p) wherein the at least one controlled constant current source 151 is further configured to be sequentially connected to each of the plurality of body surface electrodes 430 between about once every 10 milliseconds and about once every 500 milliseconds; (q) wherein the at least one controlled constant current source 151 is further configured to be sequentially connected to each of the plurality of body surface electrodes 430 between about once every 100 milliseconds and once about every 300 milliseconds; (r) wherein the data acquisition or recording device 60A further comprises amplifiers 145 and filters 143 configured to amplify and filter the sensed electrical signals; (s) wherein the amplifiers 145 and filters 143 are configured to at least one of amplify, bandpass filter, notch filter, low-pass filter, high pass filter, and digitally filter the sensed electrical signals; (t) wherein the at least one three-dimensional location of at least one of the catheter or medical device electrodes located within the patient's body 5 and the at least portion of the volume is determined with an accuracy of about 2 mm or less; (u) wherein a number of the plurality of body surface electrodes ranges between about 2 and about 128, or between about 4 and about 64, or between about 8 and 32; (v) wherein a number of the plurality of body surface electrodes 430 ranges between about 4 and about 32; (w) wherein a number of the plurality of catheter electrodes ranges between about 1 and about 256; (x) wherein a number of the plurality of catheter or medical electrodes ranges between about 8 and about 128, or between about 16 and about 64; (y) wherein the at least one three-dimensional model or matrix of the volume is generated according to at least one of the patient's body mass index (BMI), sex, weight, size, and age; (z) wherein the medical device or catheter 110, or portion thereof, is configured to be inserted into a patient's vein or artery and moved therethrough or therein; (aa) wherein the medical device or catheter 110, or portion thereof, is configured to be inserted into one of a patient's coronary artery, brain, throat, esophagus, stomach, liver, urinary tract, colon, orifice, or other body organ, tissue or passageway.

As regards the aforementioned volume or region of interest comprising voxels, voxels are individual volume elements, and each voxel represents a value in a three dimensional space, which in turn can correspond to a pixel for a given slice thickness. Voxels are frequently used in the visualization and analysis of medical data, such as MRIs.

In one embodiment of a controlled constant current navigation, positioning and imaging system, and in respect of a volume or region of interest encompassing heart 10, the volume or region of interest has dimensions of 15 cm×15 cm×15 cm, and individual voxels having dimensions of 1 mm×1 mm×1 mm, for a total of 3,375,000 voxels. During navigation, receiving or sensing electrode 3D positions within the volume are associated with specific voxels within the volume, more about which is said below.

Figure 5:
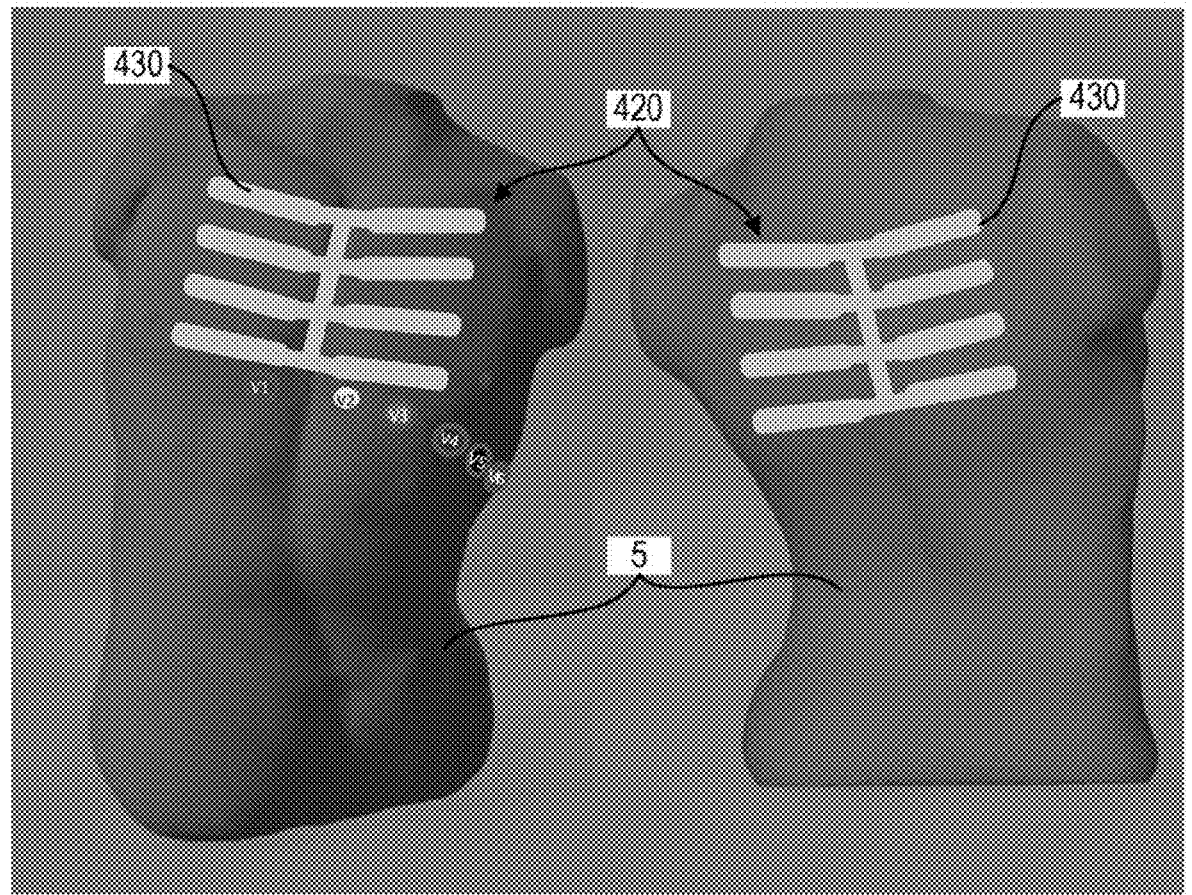
FIG. 5 shows one embodiment of body surface electrodes 430 positioned on a human torso or body 5.
Figure 6:
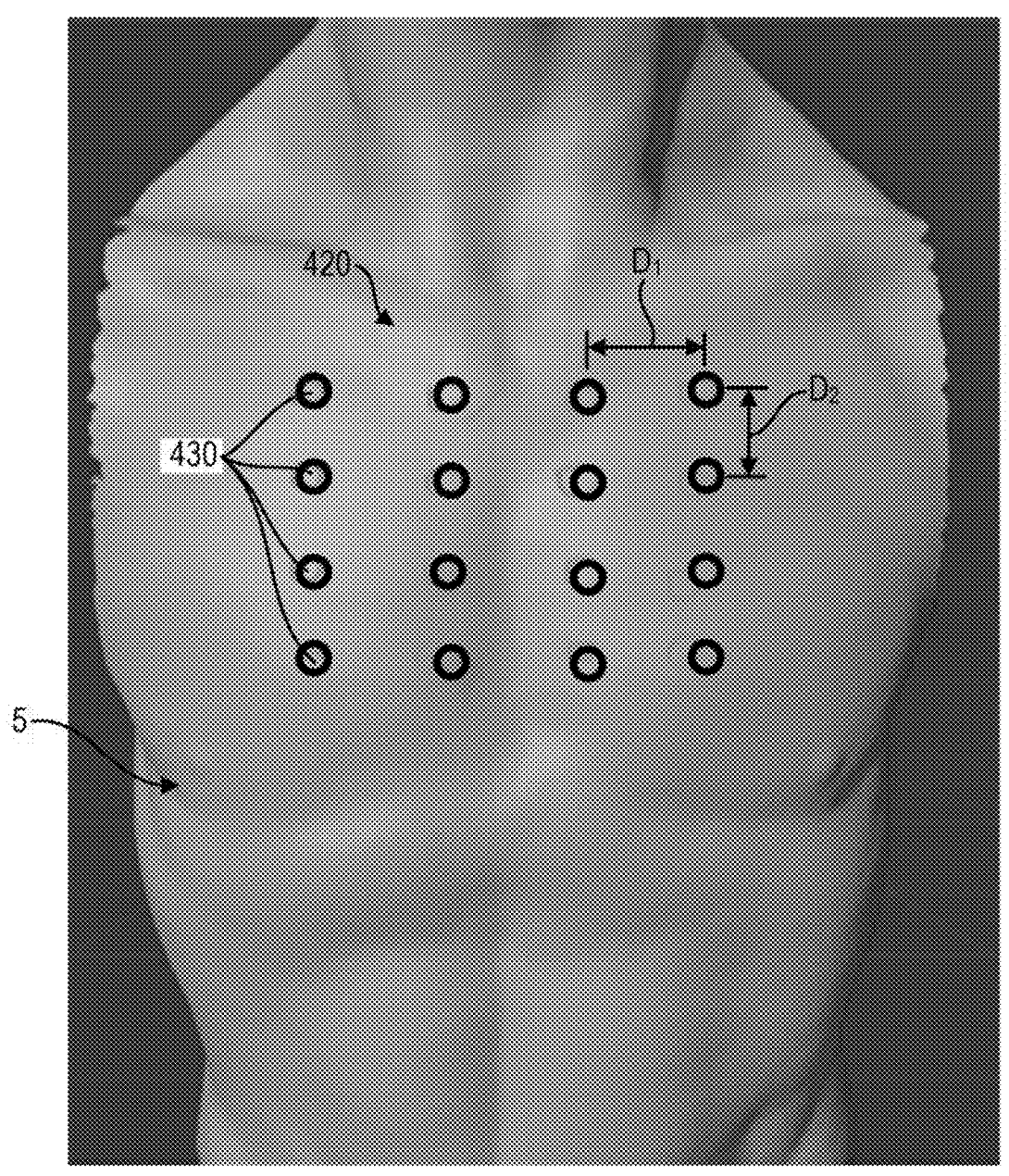
FIG. 6 shows one embodiment of an array of body surface electrodes 430 positioned on a human torso or body 5.
Figure 7:
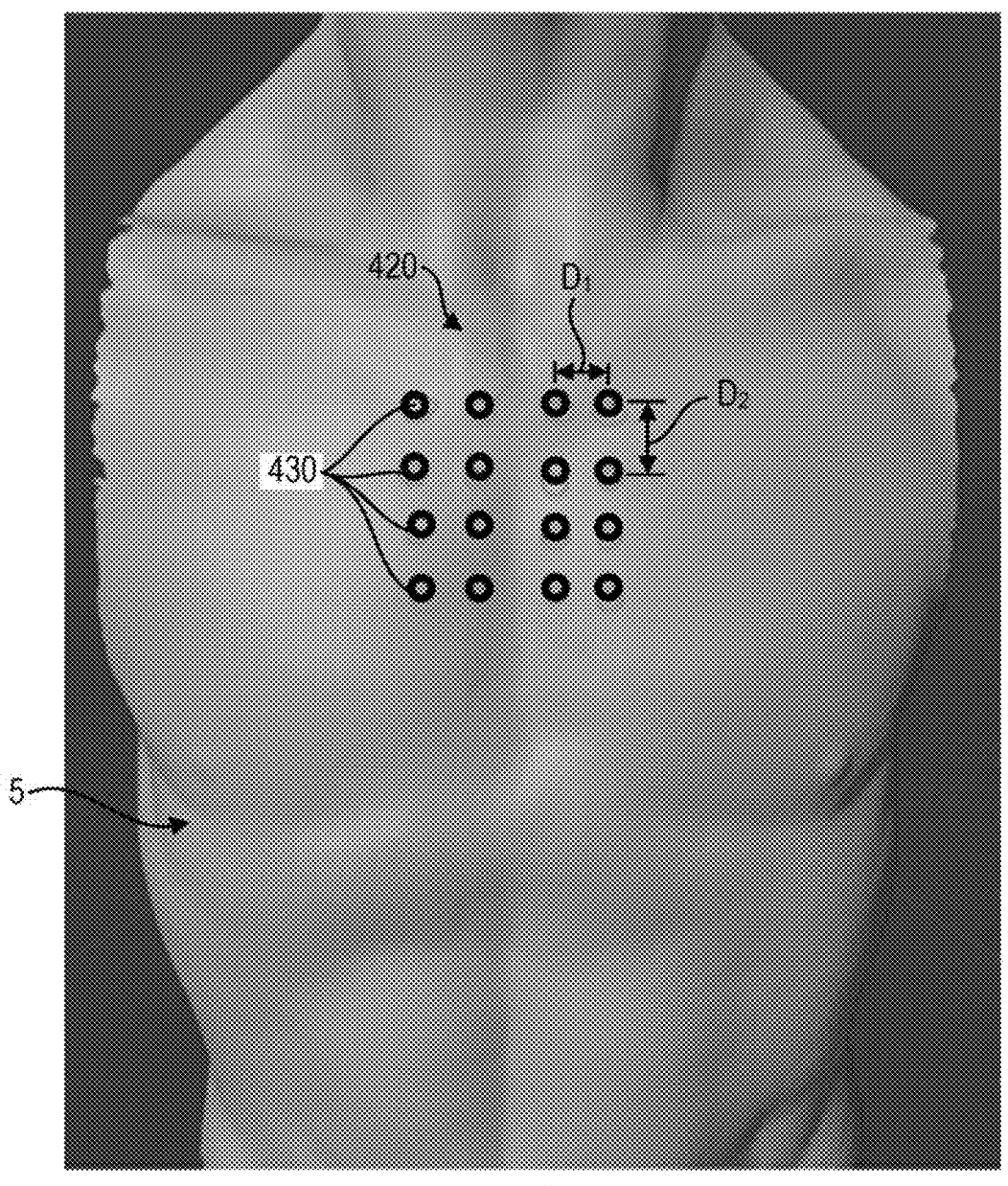
FIG. 7 shows another embodiment of an array of body surface electrodes 430 positioned on a human torso or body 5.

Some Theoretical and Practical Aspects of Controlled Constant Current Navigation, Positioning and Imaging Referring now to FIG. 5, the controlled constant current scanning method can be done quickly, and by way of non-limiting example is capable of providing the positions of 12, 24, 36, 48, 64, 128 or other numbers of independent catheter or medical device electrodes about every 200 msec, by, for example and in one embodiment, exploiting state of the art machine learning techniques to define a 3D space or volume after extracting a compensatory transformation matrix to eliminate distortions. Other time sampling or presentation intervals are also contemplated, such as about every 25 msec., about every 50 msec., about every 100 msec., about every 300 msec., about every 400 msec., about every 1 second, or any other suitable or useful time interval.

Controlled constant current technology can interface with the Ablamap amplifier (see, e.g., FIGS. 18 and 19), and display results as 3D reconstructions of any catheter or medical device geometry (e.g., a basket catheter, a pulsed field ablation (PFA) catheter, a loop ablation catheter, a pulse field ablation catheter, a coronary or CS catheter, an ablation catheter, and other medical devices and device geometries) in real time or near-real-time together with the results of Ablacon's Ablamap EGF mapping system.

Controlled constant current technology can also be used to generate an anatomical shell (for example by using basket catheter, pFix catheter or ablation catheter outlines in the heart 10), and onto which mapping results created with the Ablamap system may then be projected.

Features of some embodiments of the controlled constant current navigation, positioning and/or imaging systems described and disclosed herein include, but are not limited to, the following: (a) employ a matrix or array of controlled constant current sources in the RF frequency range, optionally combined with bioelectric signals (e.g., extracted QRST complexes), to provide accurate and precise imaging of the heart 10; (b) no requirements for position triangulation, and the provision of absolute 3D coordinates for intracardiac catheters and other medical devices 110; (c) fast scanning to provide the position of, for example, 128 independent catheter electrodes every 200 ms (or other time interval); (d) compensate for heart atrial movements with heartbeat, breathing, and patient movements using, for example, a CS catheter; (e) generate an anatomical shell using basket, lasso, ablation catheters or other medical devices 110 and project and display mapping results onto a display 64 in real-time or near-real-time, and (f) interface with an amplifier system 60A and computer 60B/300 for 3D reconstruction of catheter geometries in real-time or near-real-time.

Figure 8:
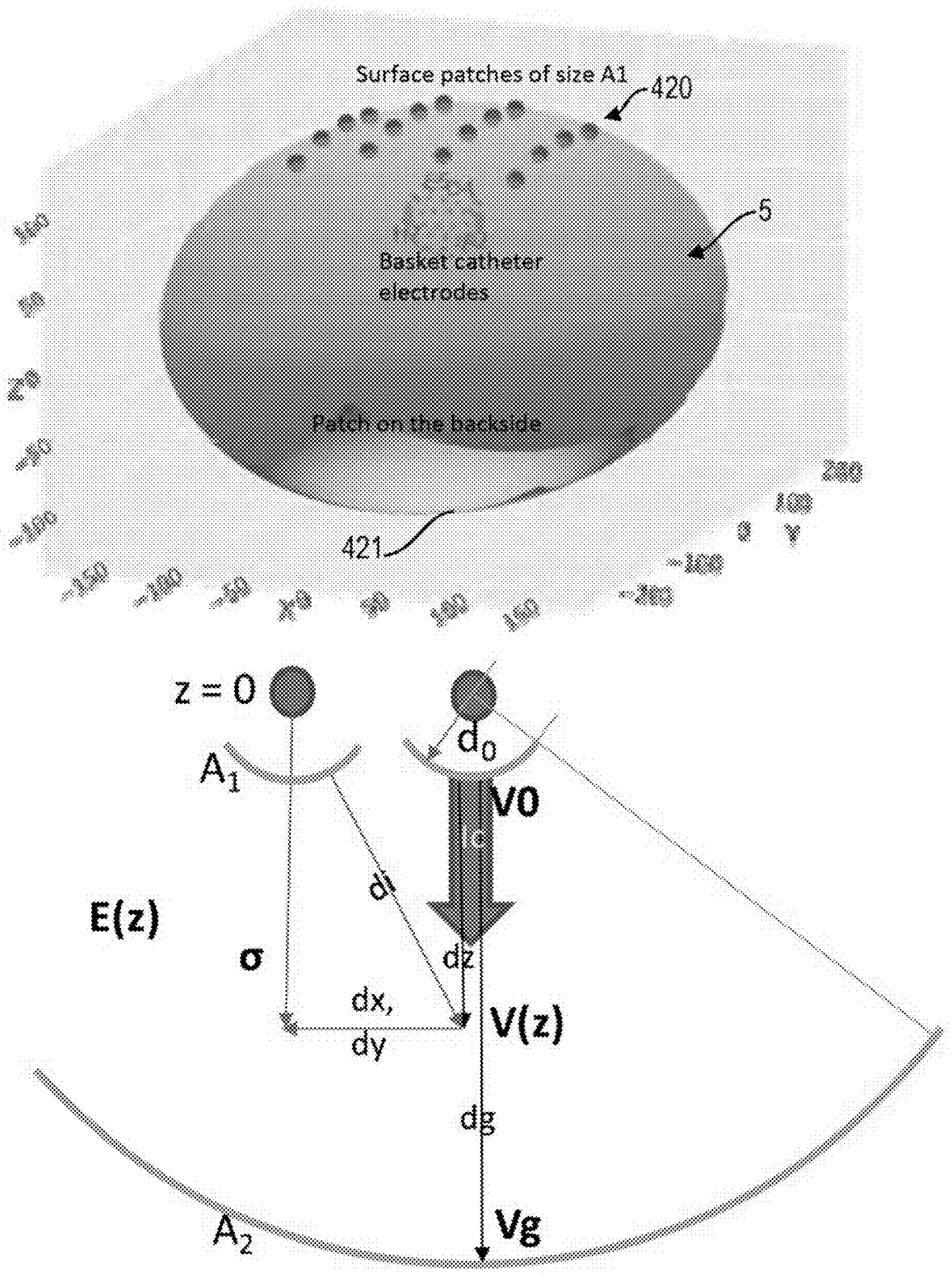
FIG. 8 illustrates some basic concepts regarding of controlled constant current navigation, positioning and/or imaging a medical device or catheter 110 inside a human body.
Figure 9:
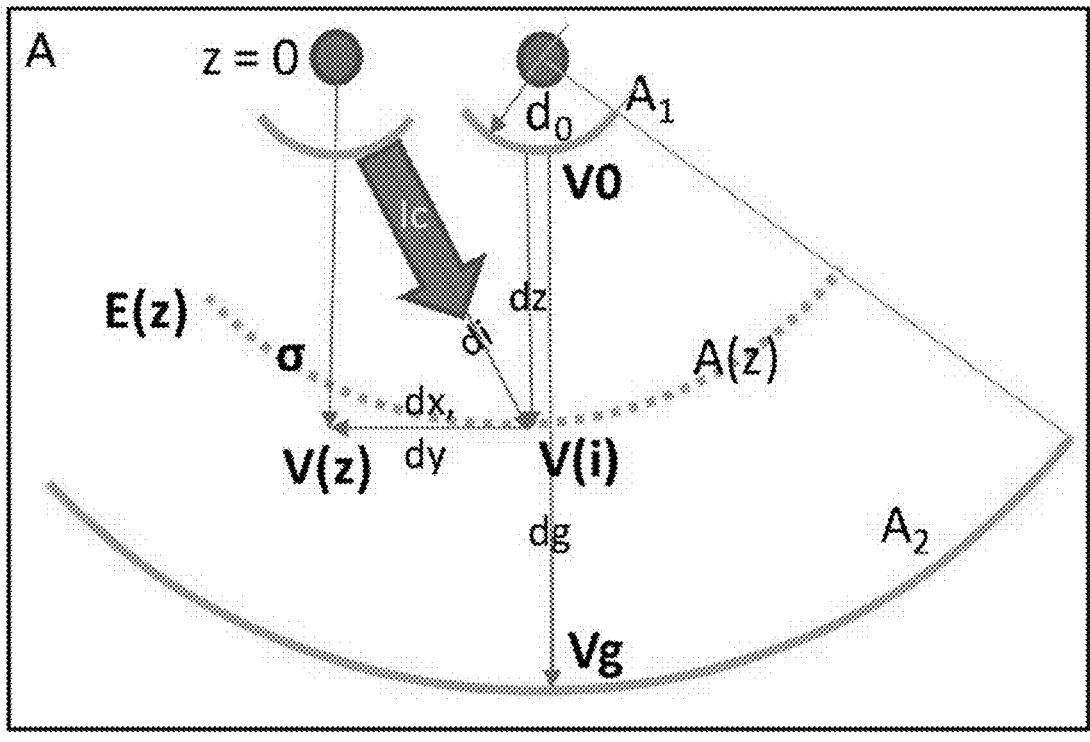
FIG. 9 illustrates the radiation theorem as it relates to controlled constant current navigation, positioning and/or imaging a medical device or catheter 110 inside a human body.

As regards basic concepts of controlled constant current navigation, positioning and/or imaging according to some embodiments, and with reference to FIG. 8, we can start by considering 16×1 cm electrode patches on the chest of size $A_1$ (100 mm² and size $s_1$ 10 mm), a body conductivity $\sigma$ (e.g., $7e^{-4}$ S/mm), and a constant current $I_c$ of 10 mA multiplexed through any surface patches of size $A_1$. A second patch on the backside of the body, at a distance of $d_g$=250 mm from $A_1$, can have a larger size $A_2$ (40,000 mm² and size $s_2$ 200 mm). In one embodiment, chest electrodes 430 are assumed to be equally spaced (4×4 electrodes in 50 mm distance) in the x (from left to right) and y (from bottom to top) directions. See FIGS. 6 and 7.

With continuing reference to FIG. 8, note that the constant current from each of the body surface electrodes 430 located on the patient's chest is typically divergent in respect of the large electrode located on the patient's backside. Consequently, for an electrode located on medical device or catheter 110 in the patient's heart 10, and which is configured to sense or record received controlled constant current signals, a strong dependence on the distance from an individual body surface electrode 430 to an electrode located on medical device or catheter 110 is likely to result.

The electric field is measured in the z-direction from ventral to dorsal inside the patient's body 5. This yields the electric field:

$$E(z) = \frac{Ic}{A(z) \times \sigma}$$

A is assumed to increase linearly from $A_1$ to $A_2$ and can be projected in the ventral direction to an infinitely small $A_0$, where the field would theoretically be infinitely strong. $A_0$ is at a distance $d_0$ from $A_1$, with $$\frac{d_0}{s_1} = \frac{d_0 + d_g}{s_2}$$

or $$d_0 = \frac{d_g}{\frac{s_2}{s_1} - 1}$$

In the following, and with reference to FIGS. 8-11, we derive the voltage measured by a catheter or medical device 110 located inside the body 5 as a function of the coordinate z, (V(z)) and discuss the scanning process and its ability to determine the precise location of the catheter electrode.

To derive the voltage function V(i) and understand its role in current scanning navigation technology, first consider the relationship between $A_1$ and A(z) according to the radiation theorem (FIG. 9) areas $A_1$ and A(z) behave like the square of the distances $d_0$ and $d_0$+z:

$$A(z) = \left(\frac{z}{d_0} + 1\right)^2 \times A_1$$

Hence, the expression:

$$E(z) = \frac{I_c}{\left(\frac{z}{d_0} + 1\right)^2 \times A_1 \times \sigma}$$

To calculate the voltage as a function of z, we integrate the electric field E(z) along the z-direction:

$$V(z) = \left(\frac{I_c}{A_1 \times \sigma}\right) \times \int \frac{1}{\left(\frac{z}{d_0} + 1\right)^2} \, dz$$

We substitute $$u = \left(\frac{z}{d_0} + 1\right),$$

then $z=d_0 \times (u-1)$, and $dz=d_0 \times du$ and rewrite the integral in terms of u:

$$V(z) = \left(I_c \times \frac{d_0}{A_1 \times \sigma}\right) \times \int \frac{du}{u^2}$$

and integrate to:

$$V(z) = \left(I_c \times \frac{d_0}{A_1 \times \sigma}\right) \times \left(-\frac{1}{u}\right) + C$$

Finally, substitute the expression for u back in terms of z:

$$V(z) = \left(I_c \times \frac{d_0}{A_1 \times \sigma}\right) \times \left(-\frac{1}{\frac{z}{d_0} + 1}\right) + C$$

Using the boundary condition that the voltage is zero at the large patch $A_2$ on the back (z=$d_g$), we can find the value of the integration constant C:

$$C = \left(I_c \times \frac{d_0}{A_1 \times \sigma}\right) \times \frac{1}{\frac{d_g}{d_0} + 1}$$

Substitute the value of C back into the expression for V(z) to obtain the final result:

$$V(z) = \left(I_c \times \frac{d_0}{A_1 \times \sigma}\right) \times \left(\frac{1}{\frac{z}{d_0} + 1} - \frac{1}{\frac{d_g}{d_0} + 1}\right)$$

When the inner catheter electrode is moved sideward small amount dx and dy:

$$di = \sqrt{dx^2 + dy^2 + dz^2} \qquad (1)$$

and $$V(i) = \left(I_c \times \frac{d_0}{A_1 \times \sigma}\right) \times \left(\frac{1}{\frac{\sqrt{dx^2 + dy^2 + dz^2}}{d_0} + 1} - \frac{1}{\frac{d_g}{d_0} + 1}\right)$$

Figure 10:
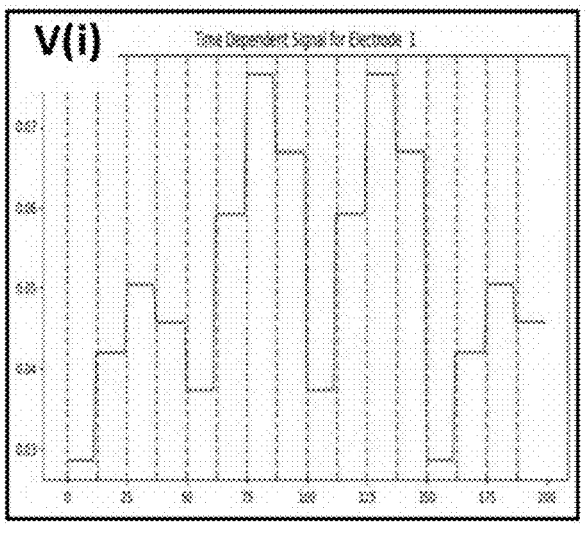
FIG. 10 illustrates example of voltages sensed by a single internal sensing or reception electrode located on medical device or catheter 110, where the 16 steps displayed therein correspond to controlled constant current signals emitted by 16 body surface electrodes and received by the single internal sensing or reception electrode.
Figure 11:
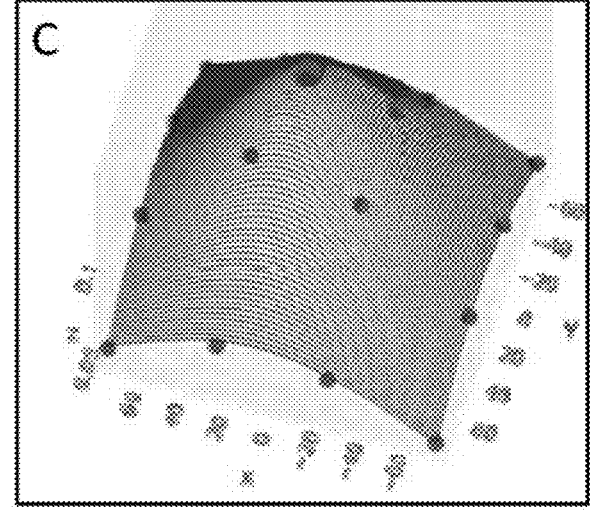
FIG. 11 shows a fit of maximum V(c) of the surface of V(i) in dependence of a 4×4 matrix of surface electrodes 430.

After scanning through all 16 surface electrodes, we obtain the recording of V(i) from any internal catheter or medical device electrode (see FIG. 10, which shows the voltages sensed by internal sensing or reception electrode 1 corresponding to each of the 16 body surface electrodes 430). Equation (1) can be solved to yield $x_c$, $y_c$ and $z_c$, the coordinates of our catheter electrode by fitting the maximum of V(c) of the surface of V(i) in dependence of the 4×4 matrix of the surface electrodes (see FIG. 11).

Since the voltage V(i) is measured between A(z) and $A_2$ it depends on current density and conductance between the A(z) and $A_2$. Because of the constant current source $V_0$ but not the current density at A(z) depends on the conductance between $A_1$ and A(z). Hence V(i) is independent on conductivity differences below the body surface electrodes and depends only on geometry.

Figure 12:
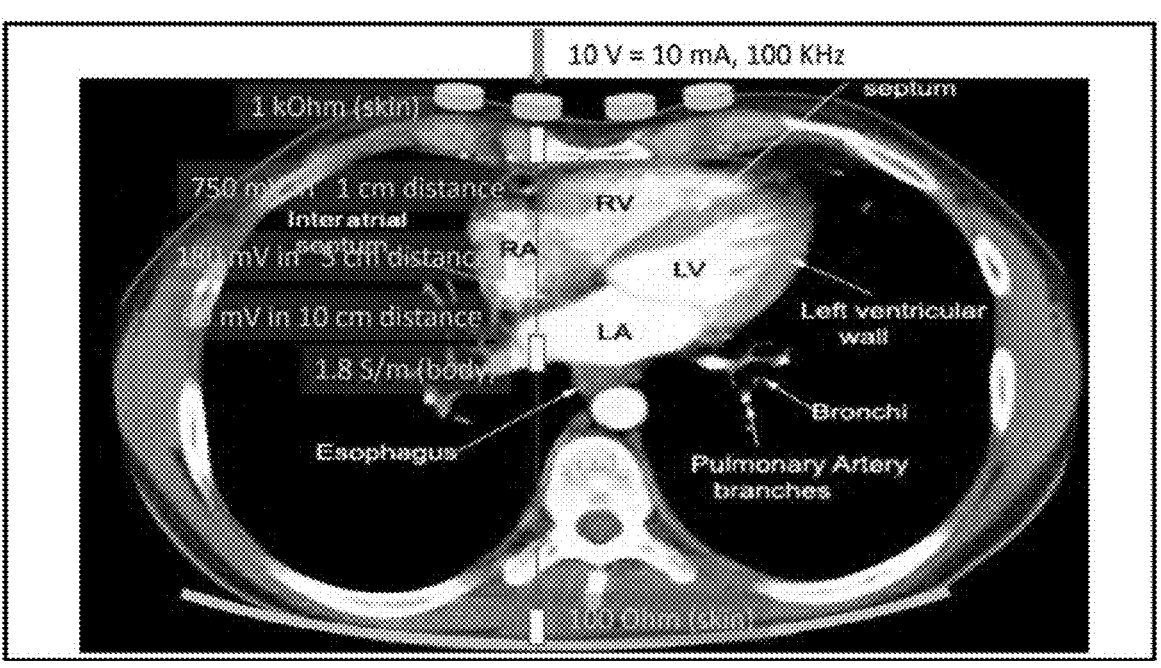
FIGS. 12 and 13 show some details regarding one embodiment of a controlled constant current scanning process, and signal detection inside the human body by electrodes located on a catheter or other medical device.
Figure 13:
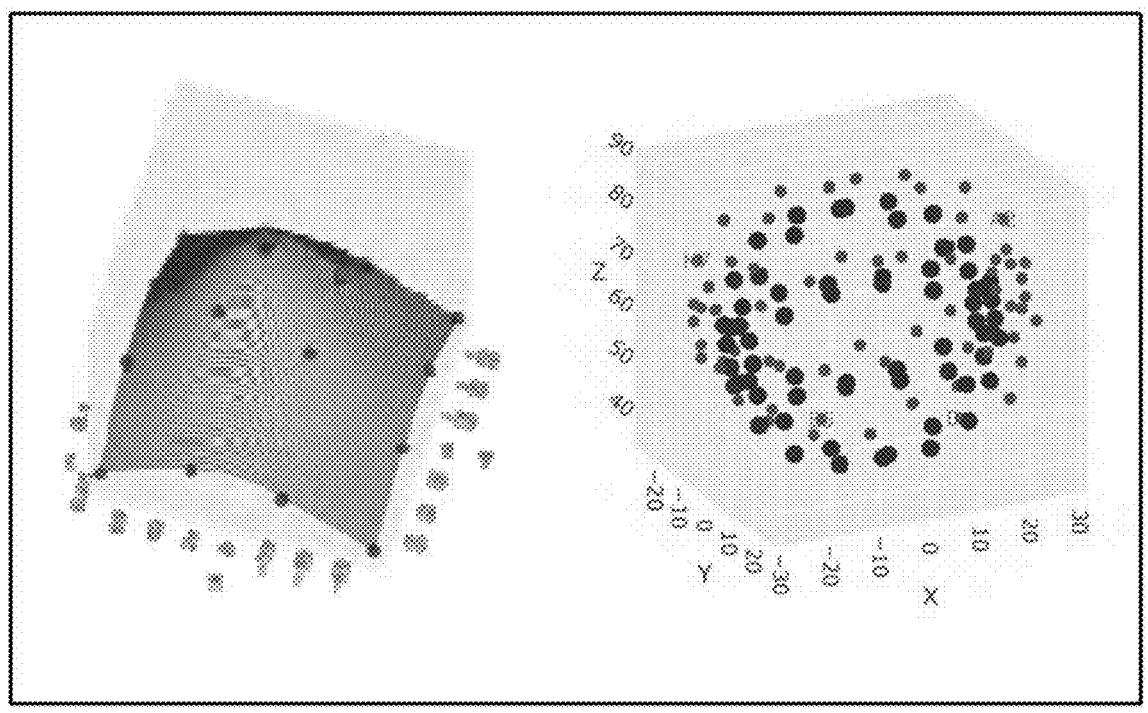

As regards some embodiments of controlled constant current scanning and constant current signal detection/sensing/reception processes, and with reference to FIGS. 12 and 13, we note and describe the following. During the scanning process, a 100 kHz constant current amplitude (or other suitable amplitude) signal is multiplexed between the 16 electrodes within a time cycle of 200 ms per scanning sweep. The resulting signal, recorded by an electrode inside the body, needs to be measured with high precision. In one embodiment, the maximum risk-free current at 100 KHz, which does not generate a sensation in the skin, is 10 mA. The electrode resistance at this frequency is between about 500 and 1000 Ohms. The navigation system aims to achieve a sensitivity of better than 1 mm. As the current jumps from one electrode to the next, the electrodes inside the body record voltage amplitudes that depend on the distance between the internal electrode located within the volume and the respective body surface electrode 430. This amplitude matrix of 16 values has a virtual maximum at the x-y location where the distance to the surface (z) is minimal.

The x-y location can be fitted into this matrix along with the virtually maximal voltage, yielding the z-value according to the derived equation for V(i). In this way, the x, y, and z values are all determined by the same fit. This method has a critical advantage: any distortion due to variable conductance values in the tissue between the electrodes is simply and simultaneously reflected in all values. By using the known dimensions of catheters with multiple electrodes, these distortions can be eliminated through simple linear transformations in the obtained 3D space.

Since the CS-catheter is usually positioned at a constant location, this signal is also suited to monitor and compensate for time-dependent shifts in the conductivities due to patient movements or changes in body hydration.

The scanning process is crucial for determining the precise location of the catheter or medical device electrode within the body. The scanning system must be capable of detecting voltage differences as small as the noise level, which we calculate according to the Johnson-Nyquist noise formula (also known as thermal noise):

$$V_{noise} = \sqrt{4 \times k \times T \times R \times B}$$

Where: $V_{noise}$ is the noise in volts, k is the Boltzmann constant ($1.38064852 \times 10^{-23}$ J/K), T is the temperature in Kelvin (body temperature: approximately 37° C. or 310.15 K), R is the resistance in Ohms, B is the bandwidth in Hertz. $V_{noise}$ is about 0.26 µV at a body temperature of 37° C. and a bandwidth of 20 kHz.

Figure 14:
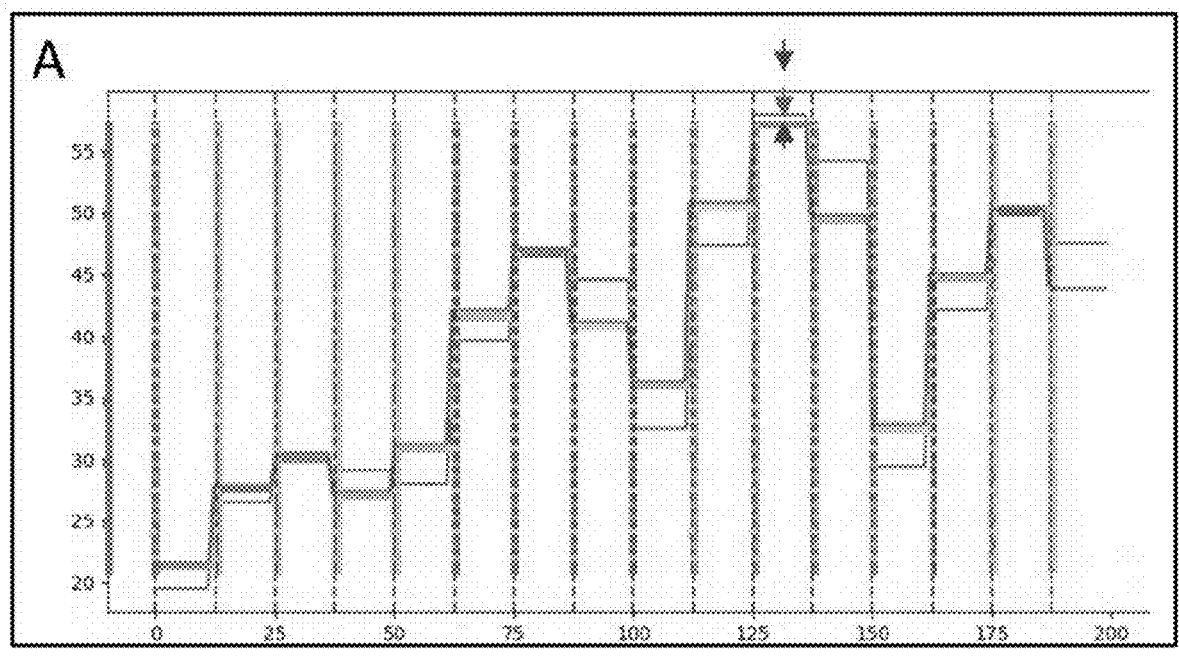
FIG. 14 shows another example of voltages sensed by a single internal sensing or reception electrode located on medical device or catheter 110, where the 16 steps displayed therein correspond to controlled constant current signals emitted by 16 body surface electrodes and received by the single internal sensing or reception electrode.
Figure 15:
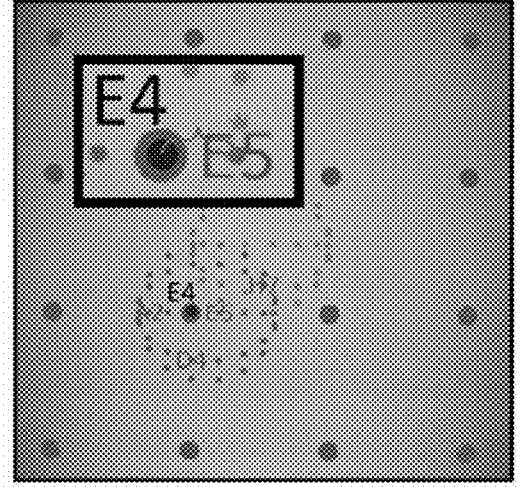
FIG. 15 shows the positions of electrodes E4 and E5.
Figure 16:
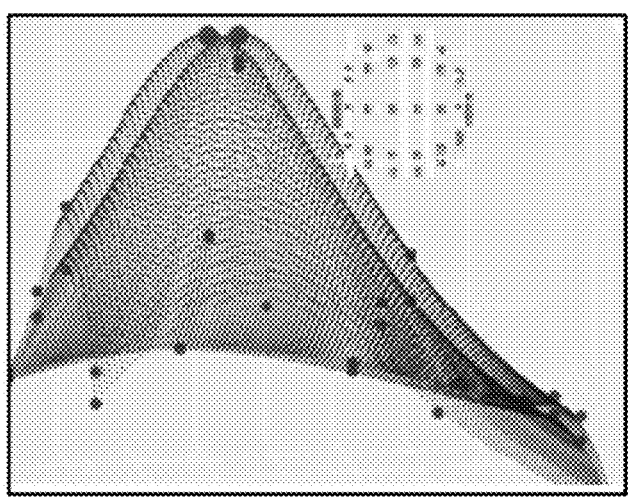
FIG. 16 shows a simulation plot.

With reference to FIGS. 14, 15 and 16, a sensitivity analysis of controlled constant current navigation, positioning and imaging technology may be carried out as follows. In one embodiment, the sensitivity of the controlled constant current scanning process is calculated as change in voltage due to a 1 mm movement in the x, y, and z-directions in relation to the theoretical noise value.

Using Eq. (1) above, we calculate the following values for a location in the center of the body:

$\Delta V_2$ change in voltage due to 1 mm movement in z-direction: 0.5 mV $\Delta V_x$ and $\Delta V_y$ change in voltage due to 1 mm movement in x and y-directions: 2.2 µV $\Delta V_x$ and $\Delta V_y$ change in voltage due to 10 mm movement in x and y-directions: 200 µV Noise level (Johnson-Nyquist noise) of 1.94 µV The calculated values for $\Delta V_x$ and $\Delta V_y$ are very close to the noise level, which could make detecting a 1 mm movement in the x and y-directions challenging. If we look at the simulation plot of FIG. 16, however, we can confirm that a voltage change occurs between electrodes E4 and E5 (see FIGS. 15 and 16), which are 10 mm apart from one another, while electrode E4 (which is located exactly below its respective body surface electrode) is indeed only at 200 µV (see yellow arrows in FIG. 14).

Figure 17:
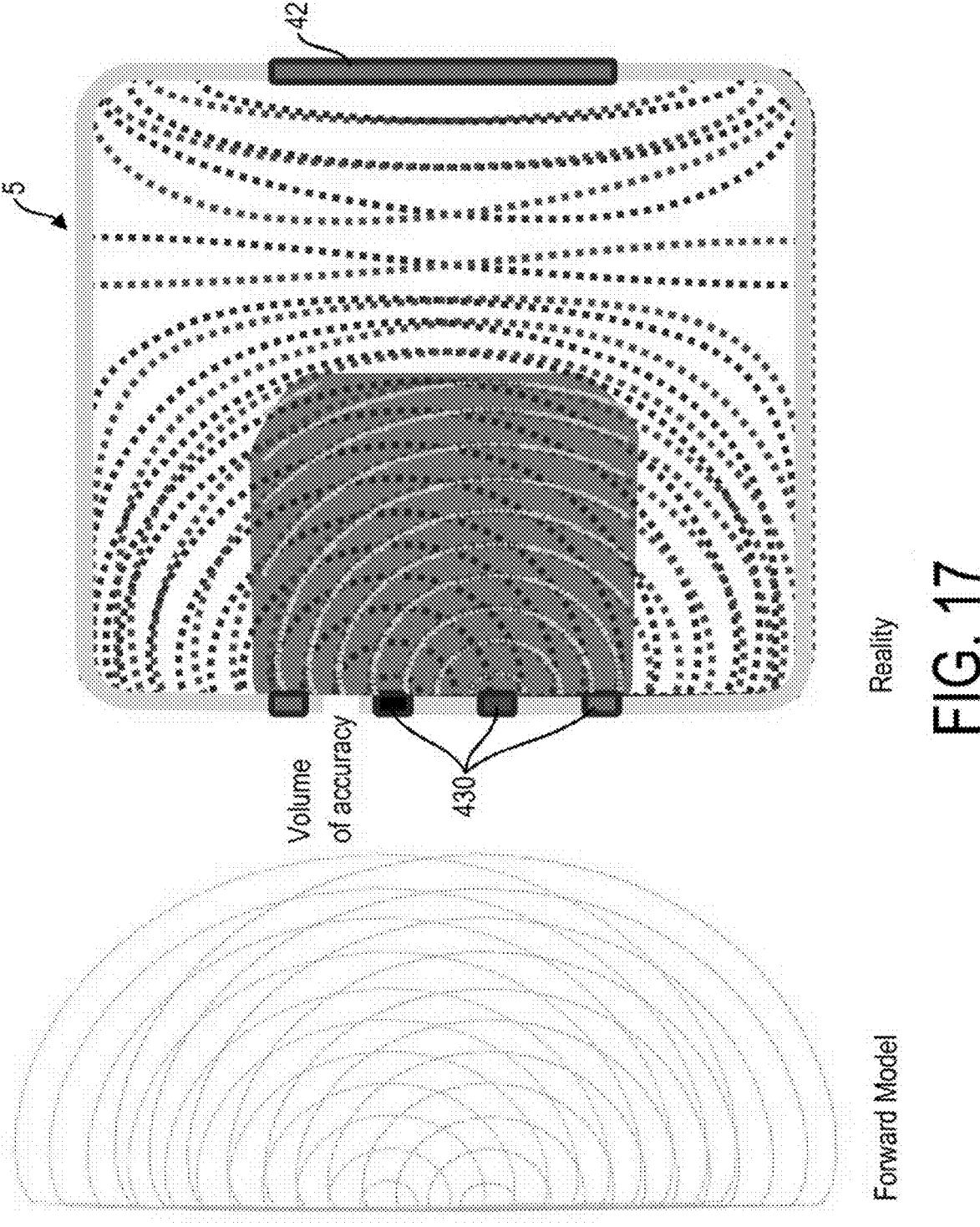
FIG. 17 illustrates the difference between a forward model electrical field computation and that which may occur in actual practice.

It is important, however, to note that the change in signals from all 16 electrodes will be relevant for the fit shown in FIG. 16. Some of the surface electrode signals show a much larger change in amplitude upon the 10 mm shift (as much as 5 mV). In consequence, the fitted distance between the electrodes E4 and E5 (see FIG. 15) yields the expected 10 mm distance very accurately and the two fits differ by several mV, which is more than 10-fold above the noise level. In summary, it is likely that in actual practice the resolution of catheter movements of the controlled constant current navigation, positioning and imaging system 100 can attain a positional accuracy of less than a 1 mm. FIG. 17 illustrates the difference between a forward model electrical field computation and that which may occur in actual practice.

Figure 18:
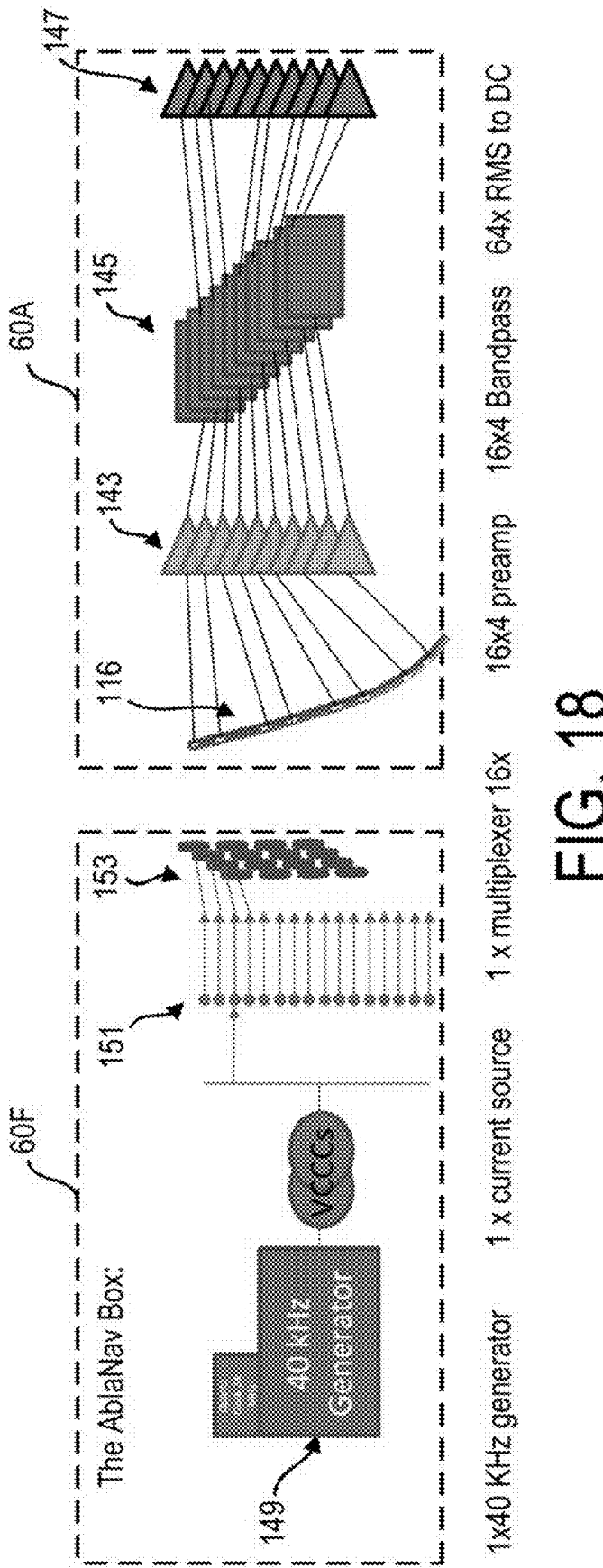
FIGS. 18, 19 and 20 show some embodiments of a controlled constant current navigation, positioning and/or imaging system.
Figure 19:
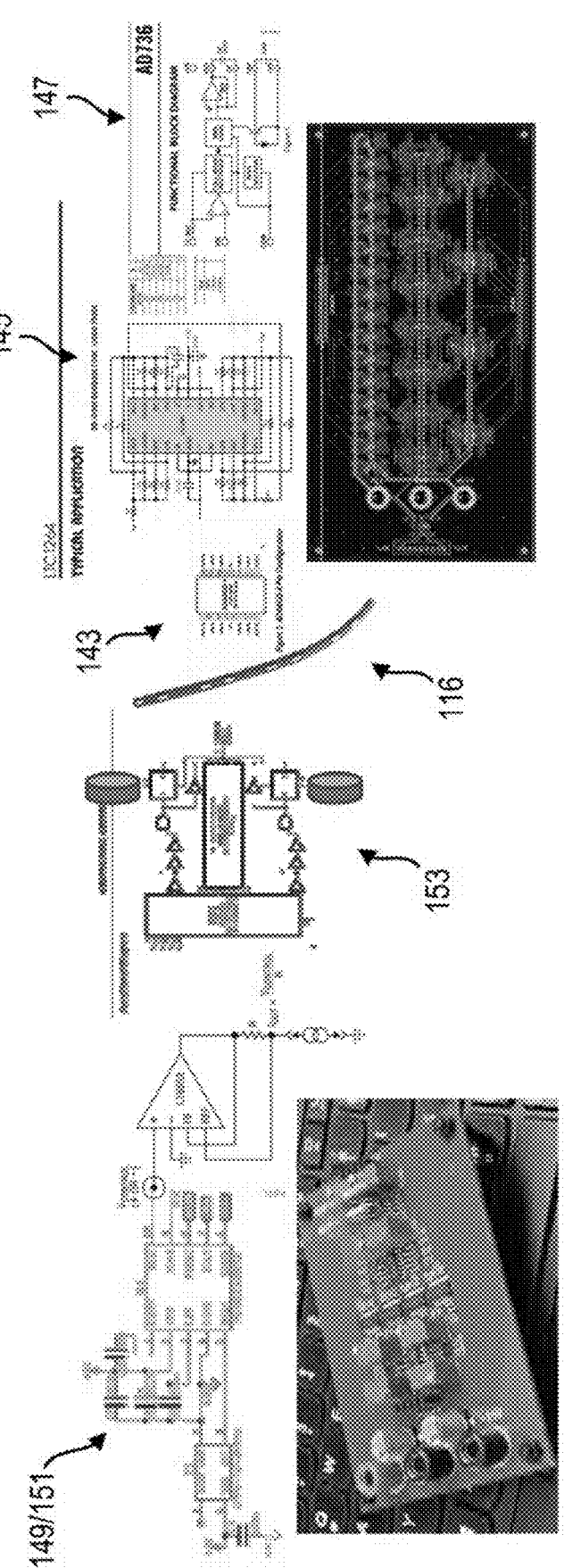

FIGS. 18 and 19 show one embodiment of an AblaNav™ controlled constant current navigation, positioning and imaging module or box, which generates high-precision, high-fidelity, controlled constant current signals and multiplexes them for transmission through body surface electrodes 430 into the volume or region of interest. As shown, the AblaNav module or box also receives, amplifies, filters and digitizes the corresponding sensed signals received from electrodes positioned on catheter or medical device 110.

Referring to FIG. 18, and in one embodiment, some parts of controlled constant current navigation, positioning and imaging system 100 may comprise a 1×40 kHz generator 149, a high-precision or high-fidelity controlled constant current source 151, a 16-channel multiplexer 153, a 16-channel preamplifier 143, a 16-channel bandpass filter 145, and a 64× RMS to DC analog-to-digital converter (ADC) 147. In one embodiment, controlled constant current source 151 is configured and/or calibrated to provide as outputs therefrom constant current signals that have an amplitude variation from a specified output value of no more than about 1% upon doubling of the electrode resistance or impedance per channel; as described above, the accuracy, controllability and fidelity of constant current outputs from current source 151 are important.

See, for example, "A Large Current Source with High Accuracy and Fast Settling" to Jiang, N., Analog Dialogue 42-10, October 2018, Analog Devices, the entirety of which is incorporated by reference herein, a complete copy of which is submitted on the filing date of this patent application pursuant to an Information Disclosure Statement filed herewith, which discloses one embodiment of a current source that may be adapted for use as a controlled constant current source as described and disclosed herein.

In some embodiments, a sufficiently accurate controlled constant current source 151 capable of transmitting low-variation output signals into a patient's body 5 is required to yield a suitable navigation signal within the volume or region of interest: Navigating with a properly configured controlled constant current source can significantly improve the precision of internal body distance measurements and navigation. One significant factor that can contribute to the efficacy and effectiveness of various embodiments of the controlled constant current navigation systems and methods described and disclosed herein is a controlled constant current source 151 that is configured to automatically adjust the overall voltages and/or current at each body surface electrode 430 so as to compensate for any potential variability in resistance or impedance at the skin-electrode interface or for differences in tissue types. This ensures that controlled constant current signals received by navigation electrodes located on medical device or catheter 110 the measurement are not influenced by variations in body surface electrode impedance variables, but instead depend to a substantial extent on the geometrical distribution of the current from the point where it is injected into the patient's body.

According to one embodiment, the system's ability to self-adjust for resistance and impedance variations enables the navigation system 60 to provide precise measurements of distances within the body 5, making it an optimal choice for such applications. This technique is particularly effective if using high-frequency alternating current (e.g., about 1 kHz to about 1 MHz), which is well-conducted by body tissues, particularly those with cell membranes, and by measuring sensed or received voltages against a reference electrode located on the patient's back.

With reference to FIG. 19, and in one embodiment and by way of non-limiting example, the following devices and components may be employed in modules 60F and 60A as follows:

For 1×40 kHz generator 149: CFDS-72-24 Mz AD9833BRMZ (Direct Digital Synthesis IC 10 b 25 MHz 28 b Tuning 10-MSOP made by Analog Devices, Inc.)

For high-precision or high-fidelity controlled constant current source 151: LT6552 3.3V Single Supply Video Difference Amplifier made by Analog Devices, Inc.

For 16-channel multiplexer 151: CD74HCT4067 5-V, 16:1, 1-channel analog multiplexer with TTL inputs made by Texas Instruments, Inc.

For 16-channel preamplifier 143: ADA4522-4 Quad 55 V, EMI Enhanced, Zero Drift, Ultralow Noise, Rail-to-Rail Output Operational Amplifier made by Analog Devices, Inc.

For 16-channel bandpass filter 143: LTC1264 High Speed, Quad Universal Filter Building Block made by Analog Devices, Inc.

For 64× RMS to DC analog-to-digital converter (ADC) 149: AD736 Low Cost, Low Power, True RMS-to-DC Converter.

Figure 20:
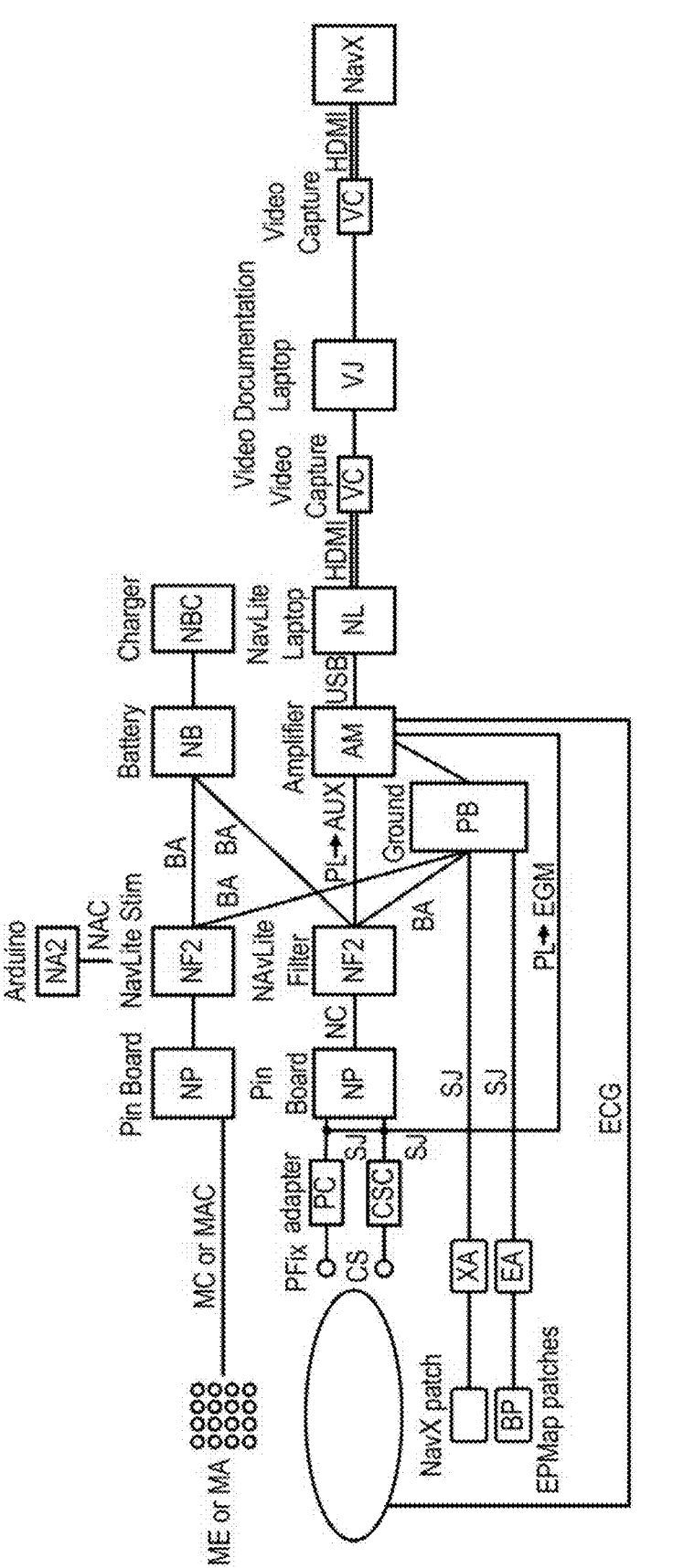

FIG. 20 shows one embodiment of an electrical circuit block diagram for a system 100 comprising various components from FIGS. 1, 3, 18 and 19, including body surface electrodes 430 (NavX patch), the AblaNav Box, and body surface electrodes for electrophysiological (EPMap patches), along with other modules and components that may be employed in a controlled constant current navigation, positioning and imaging system.

Figure 21A:
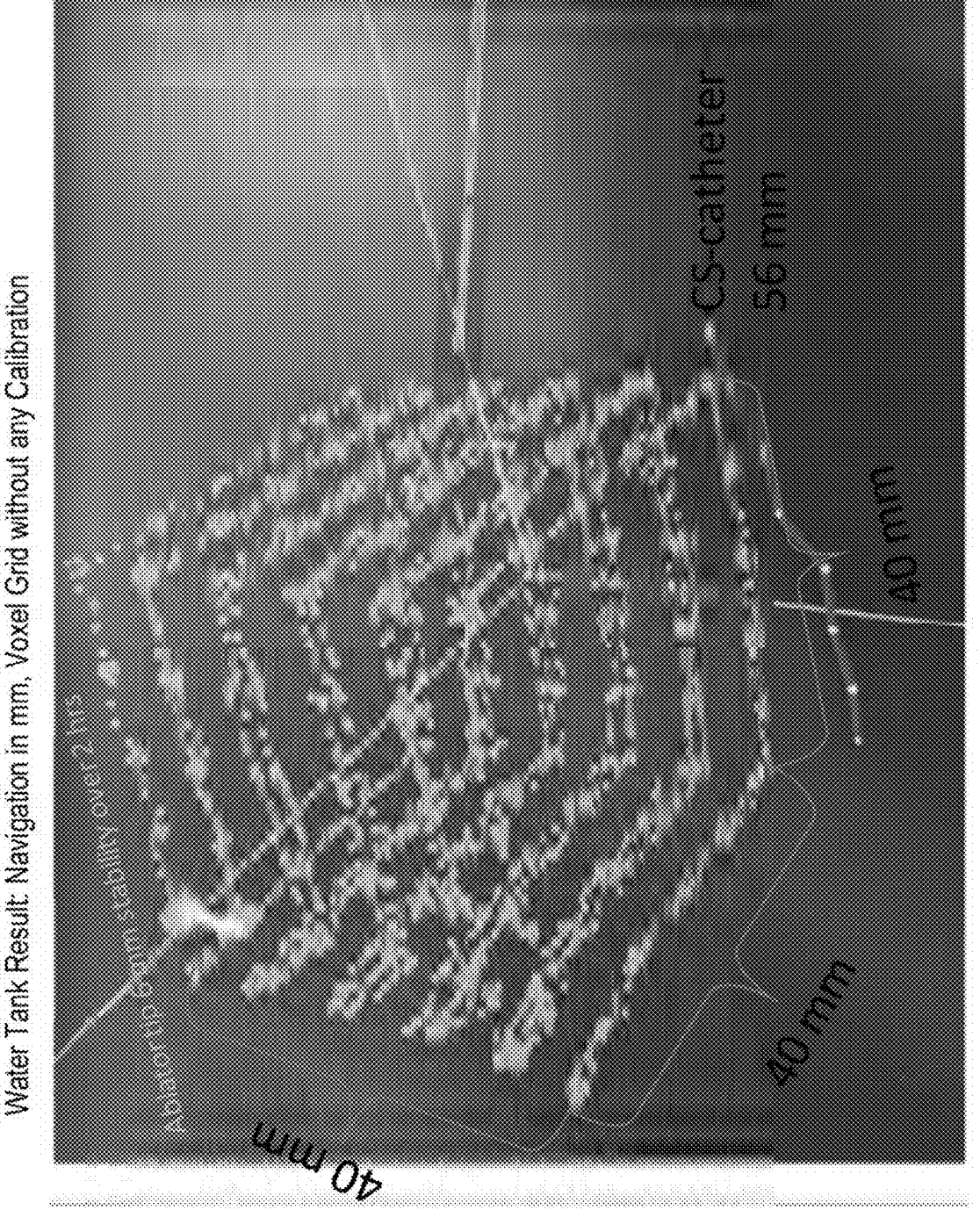
FIGS. 21A and 21B show actual results obtained in a water tank with one embodiment of a controlled constant current navigation system.
Figure 21B:

FIGS. 21A and 21B show water tank results achieved using the AblaNav module, without calibration. FIG. 21A shows the results of precision and drift tests to determine the localization accuracy of system 60/100 in a 28 cm water tank with 16 electrodes arranged in a 4×4 array with 5 cm spacing on one side, and a 20×20 cm large electrode on the other side. The dark blue structure in FIG. 21A represents a static decapolar catheter located at a distance of approximately 50 mm from the electrode matrix. The small white structure in the upper left-hand corner of FIG. 21A represents a quadripolar catheter, which was oriented perpendicular to the matrix. Only two electrodes on the tip of the quadripolar were captured. Each light blue dot in FIG. 21A represents one of the electrode positions captured every 10 seconds over the course of one hour. A robotic arm having the quadripolar catheter mounted thereon was instructed to move in sequential 40×40 mm square outlines at different heights to achieve the resulting cubical shape shown in FIG. 21A. FIG. 21B shows a 1 mm voxel grid scale (small black and red squares) compared with recorded data. FIG. 21B illustrates that a high degree pf accuracy in 8 mm robot movement steps in the 3D representation is provided by the navigation system 60/100.

Figure 22:
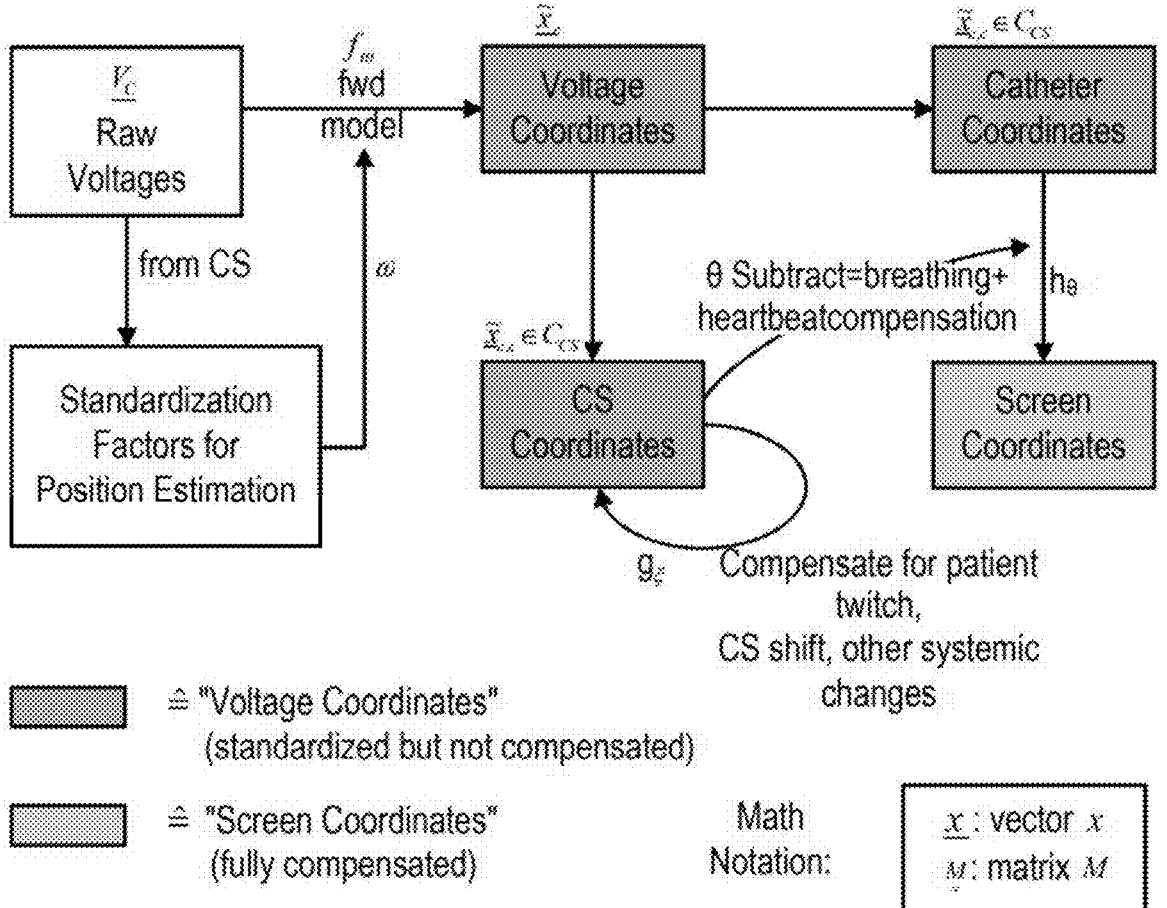
FIG. 22 shows a flow diagram for pseudo-code corresponding to one embodiment of a method of controlled constant current navigation of a medical device or catheter inside a human body.

Some Embodiments of Pseudo-Code for Controlled Constant Current Medical Device Navigation, Positioning and Imaging Referring now to FIG. 22, and in accordance with one embodiment, there are now described various aspects and details of the steps and calculations that can be used to navigate, position and/or image a medical device or catheter 110 inside a human body using a controlled constant current system (or current scanning system) as described and disclosed herein. FIG. 22 shows a block diagram for performing controlled constant current or current scanning navigation, positioning and/or imaging. The following accompanying pseudo-code and details provide further details regarding the block diagram of FIG. 22 and its operation.

Nomenclature

C: Set of catheter channels (index)

$C_{CS} \subset C$: Set of CS (current scanning or constant current source scanning) channels (subset of C)

$C_q \subset C$: Set of other catheter channels (e.g., ablator)

$\underline{V}_c \in \mathbb{R}^{16}$: 16-dimensional voltage fingerprint measured by catheter electrode c $f_\omega: \mathbb{R}^{16} \to \mathbb{R}^3$: Position estimation function ("lookup"), with standardization parameters $\omega$ from CS $\underline{\tilde{x}}_c \in \mathbb{R}^3$: Shorthand for $f(\underline{V}_c) \triangleq$ direct position estimation from pure voltage profile which will include all sorts of breathing/heartbeat effects $\underline{x}_c \in \mathbb{R}^3$: Shorthand for $g(\underline{\tilde{x}}_c) \triangleq$ "screen coordinate" after compensation $\underline{z} = g_\xi[\langle \underline{\tilde{x}}_c \rangle_{c \in C_{CS}}]$: "Zero point" on the screen computed from the average of the current CS electrode position estimates, compensates for shifts by $g_\xi$ $g_\xi: \mathbb{R}^3 \to \mathbb{R}^3$ (working on CS position estimates): a function parametrized by $\xi$ that will compensate the following cases:

(A): Patient movements beyond breathing and heartbeat (B): CS catheter displacement (C): Other effects such as blood pool alterations from irrigation Example of General Pseudo-Code for Medical Device Navigation Important Concept: \Estimate from the Rolling Past 60 Seconds:

$\bar{z}_{-60}^{0} := \langle \underline{z} \rangle_{t-60s:t}$: Average zero point.

$\underline{H}_{-60}^{0} := \text{hist}_{t-60s:t}(\underline{z})$: Histogram of zero point values/ "usual trace due to resp. & #3"

Global shift vector $\underline{d} = \underline{0}$ in the beginning

↳

$$\overset{\text{"but not"}}{\downarrow}$$
$$(A)\backslash(B) \Rightarrow \bar{z}_{-120}^{-60} = \bar{z}_{-60}^{0} \text{ and } \underline{H}_{-60}^{0} \neq \underline{H}_{-120}^{-60}$$

$(B)\backslash(A) \Rightarrow \bar{z}_{-120}^{-60} \neq \bar{z}_{-60}^{0}$ and $\underline{H}_{-60}^{0} \approx \underline{H}_{-120}^{-60}$ $(C) \Rightarrow$ drift of $\bar{z}$ and $\underline{H} \Rightarrow$ update and apply $\underline{d}$ $\notin$ (A) and (B)$\Rightarrow$problem.

↳ In every case:

Try to estimate new $\underline{z}$ and shift

Update $\xi$ and maybe global translation

Worst case: ask for "patient reconfiguration"+60 s recalibration $h_0: \mathbb{R}^3 \rightarrow \mathbb{R}^3$ $\tilde{\underline{x}}_c \mapsto \tilde{\underline{x}}_c - \underline{z}$ The "position correction function" compensating:

respiratory "cycle" shifts heartbeat "cycle" shifts by subtracting the stabilized current position estimate of the CS zero point One Embodiment of a High-Level Navigation Method:

Beginning of procedure: Insert CS catheter

Start 60 sec calibration phase:

Ensure no patient movements except breathing and heartbeat

Measure mean and std of voltages seen by CS: $\omega = \{\mu_{CS}, \sigma_{CS}\}$, where $\mu_{CS} = \langle \underline{V}_c \rangle_{c \in C_{CS}}$ and $\sigma_{CS} = \text{std}(\underline{V}_c)_{c \in C_{CS}}$ With $\omega$, define $f_\omega$ to "standardize" the measured voltages for the precomputed forward model After 60 sec calibration phase, compute.

Rolling parameters $\xi$ for CS stabilization

Real-time parameters $\theta$ for "zeroing" everything to CS zero-point

If patient movement/matrix shift/CS shift/other systemic shift detected:

Re-compute $\xi$

Continue to apply compensated correction $h_\theta$ to position estimates

In the foregoing computations and steps, electrical signal values expected to be received by sensing or receiving electrodes located on medical device or catheter 110 within the volume or region of interest are generated for comparison to the controlled constant current signals that are actually received by sensing or receiving electrodes located on medical device or catheter 110 within the volume or region of interest. In generating such expected values, a model of the volume or region of interest comprising voxels (e.g., a volume or region of interest having dimensions of 15 cm×15 cm×15 cm, and individual voxels having dimensions of 1 mm×1 mm×1 mm, for a total of 3,375.000 voxels) is generated. The model of the volume or region of interest may be configured to take into account numerous factors associated with the particular patient at hand, such as the patient's age, size, sex, body mass index (BMI), fatness, leanness, or thickness of tissue, musculature, bone characteristics, and/or cardiac characteristics (e.g., cardiomyopathy, etc.).

Example Pseudo-Code for the Generation of Expected Signal Values $$\text{Define boundaries of volume of interest}: \left. \begin{matrix} W \text{ (width)} \\ H \text{ (height)} \\ L \text{ (length)} \end{matrix} \right\} \text{ in mm}$$

Define resolution s (in mm)

Define N coordinates (x, y, z) for each body surface electrode

Define shape/size of each body surface electrode

Define location(s)+shape/size of one or more "back pitch" electrode

Define a physical model for a voltage field, e.g.

$$V(x, y, z) = d(x, y, z) / \left\| \begin{pmatrix} x \\ y \\ z \end{pmatrix} - \begin{pmatrix} a \\ b \\ c \end{pmatrix} \right\|$$

where d is a modulator and $$\begin{pmatrix} a \\ b \\ c \end{pmatrix}$$

are the coordinates of the respective body surface electrode being active (1) Allocate memory for each voxel inside the boundaries defined above, each voxel having the size of a cube with width s, and N voltage float values (2) For each voxel in the volume of interest:

For each body surface electrode:

(a) Compute the expected voltage from the physical model at this location (b) Store this information in the allocated memory for the respective voxel with its coordinates and the respective body surface electrode.

Keep this in memory for further use or persist to storage for later use (caching)

Example Pseudo-Code for Estimating 3D Coordinates from a Pre-Calculated Voxel Model Require:

Memory allocation for pre-calculated voxel model

A key-value data structure suitable for lookup, e.g. dictionary, hash map, k-d-tree. Key: voltages, value: voxel Given a set of N floating point numbers corresponding to N voltage values, query the data structure to find the index of the element closest to the measurement.

Look up the voxel corresponding to this index.

Return the (x, y, z) coordinates of this voxel.

To generate the pre-calculated voxel model (or volume, or region of interest), and in one embodiment, a finite element simulation and analysis is carried out as a pre-calculation step. By way of example, the volume or region of interest is divided into finite elements comprising 1 mm cubes, and for each cube a calculation of its expected voltage value is performed. These voltage values and their corresponding locations can then be stored in an efficient lookup table. At runtime during navigation of the medical device, voltage "fingerprints" sensed by electrodes on catheter or medical device 100 are compared to expected voltage values in the lookup table to find corresponding finite element values, which by construction all have 3D spatial coordinates corresponding thereto.

Example Pseudo-Code for Coronary Sinus (CS) Catheter Shift Detection

Require:

Minimum duration of observation T (can be rolling window)

A threshold value θ

Memory allocation to store voltage values for each CS electrode

Window of size w around R peaks to use as "fingerprint"

(1) Initialization

Detect R peaks in the observation T.

Extract windows w around each such R peak.

Store voltage values measured by each CS electrode during these windows.

Keep these as a reference for (2).

(2) Online detection

For the most recent rolling window of observations, repeat steps from (1) and compare them with previously stored values (reference values).

This comparison could be

Via a neural network

Euclidian distance

Other distance metric (D): If the comparison results in exceeding the threshold θ, report CS shift.

Constant Current Navigation, Positioning and Imaging without Generating Estimated Signal Values In another embodiment, no generation of expected signal values for a volume or region of interest is required for medical device navigation, positioning, or imaging using controlled constant current transmitted signals. That is, step 403 and portions of step 413 relating to expected electrical signal values in FIG. 4 are eliminated in such an alternative embodiment, which reduces the computational burdens associated with successful navigation of medical device or catheter 110. This of course requires a different or modified algorithm to compute the 3D coordinates of catheter or medical device electrodes on the basis of the constant current signals transmitted by body surface electrodes 430. Here, no use of a pre-computed voxel model of the volume or region of interest is employed, and instead an optimization problem is solved at runtime during navigation, positioning and/or imaging. Below is set forth one example of pseudo-code for such an alternative method using optimization techniques for navigation, positioning, or imaging a medical device inside a patient's body without employing a pre-computed voxel model of the volume or region of interest.

Given y-voltage measurements for all 16 matrix electrodes voltage model=forward model $h(x):R^3 \to R^{16}$ (see below)

We can solve the optimization problem $$\hat{x} = \arg\min_x \|h(x) - y\|$$

by running the following iterative least squares solver:

1. Choose initial guess $x_0=(0, 0, -20)$ or the previous position. k=0

2. Compute Jacobian matrix $$J_k = \begin{bmatrix} \dfrac{\partial h_0(x)}{\partial x_x} & \dfrac{\partial h_0(x)}{\partial x_y} & \dfrac{\partial h_0(x)}{\partial x_z} \\ \dfrac{\partial h_1(x)}{\partial x_x} & \dfrac{\partial h_1(x)}{\partial x_y} & \dfrac{\partial h_1(x)}{\partial x_z} \\ \vdots & \vdots & \vdots \end{bmatrix}$$

3. Update position estimate $$x_{k+1} = x_k + \Delta x$$

where $$\Delta x = \text{solve}(-J_k, h(x_k) - y)$$

is solved in a least squares sense:

$$h(x_k) - y = J_k \Delta x$$

$$\Delta x = -(J_k^T J_k)^{-1} J_k^T (h(x_k) - y)$$

4. if stopping condition $\|dx\|<0.1$ is not satisfied and k≤16, increment k and repeat from step 1

Voltage Model $$h_i(x) = \frac{v_{0_i}}{\frac{\|x - r_i\|}{d_0} + 1} - \frac{v_{0_i}}{\frac{\left\| x - \left( r_i + \begin{bmatrix} 0 \\ 0 \\ -2d_g \end{bmatrix} \right) \right\|}{d_0} + 1} - \frac{v_1}{\frac{x_z + d_g}{d_1} + 1} + v_1$$

x denotes the position in $R^3$ $r_i$ denotes the matrix electrode position in $R^3$ $v_{0_i}$ denotes the voltage level at the matrix electrode $v_1$ denotes the voltage level at the back electrode $d_0$ denotes the matrix electrode size $d_1$ denotes the back electrode size $d_g$ denotes that distance between matrix and back electrode See also, for example, N. Sirola, "Closed-form algorithms in mobile positioning: Myths and misconceptions," 2010 7th Workshop on Positioning, Navigation and Communication, Dresden, Germany, 2010, pp. 38-44, doi: 10.1109/WPNC.2010.5653789, the entirety of which is incorporated by reference herein, a complete copy of which is submitted on the filing date of this patent application pursuant to an Information Disclosure Statement filed herewith.

Some Examples of Machine Learning and Artificial Intelligence Methods for Use in Controlled Constant Current Navigation, Positioning and Imaging The computations and steps outlined and described above may be carried out in conjunction with a number of different machine learning or artificial intelligence methods (which include neural networks), a few of which are now described. The field of artificial intelligence, neural networks, and machine learning is wide, rich, varied and burgeoning, and so those skilled in the art will understand after having reviewed the specification, drawings and claims hereof that many different variations, permutations, and combinations of such techniques that are not explicitly described and disclosed herein may be employed successfully in conjunction with the controlled constant current navigation, positioning and imaging systems, devices, components described and disclosed herein.

Artificial Neural Networks and Feed Forward Networks

The goal of a feedforward network is to approximate some function f*. For example, for a classifier, y=f*(x) maps an input x to a category y. A feedforward network defines a mapping y=f(x; θ) and learns the value of the parameters θ that result in the best function approximation.

During neural network training, for each example x from the training data, the parameters θ are adjusted, so that the output of the network of the given example x is close to the expected label y. This difference between the output and the expected label y is called loss. The adjustment of θ is done using a gradient-learning approach.

A feedforward neural network consists of multiple layers, with a layer being defined as multiple neurons. All neurons of one layer are connected with all neurons of the next layer. Those neuron to neuron connections are weighted. Each neuron also has a bias, which is just a scalar value. The output of a neuron is the sum of the weighted inputs $\Sigma_i^n w_i x_i$ plus the bias b. This output is then fed into a non-linear activation function a, so that the network can also learn non-linear functions. The overall function of a single neuron is defined as:

$$a\left(\sum_i^n w_i x_i + b\right),$$

with n being the number of neurons in the previous layer.

Convolutional Neural Networks

Feed forward networks have the major drawback that each neuron has its own connection, i.e., weight to each neuron in the next layer. Using multiple layers with multiple neurons lets the number of weights explode very quickly.

Convolutional neural networks make use of weight sharing. Convolutional layers consist of a set of kernels (also called filters) that are convolved with the input. A convolution can be seen as a dot product between the kernel and the input. All values of the input are multiplied by their corresponding value (also called weighting) in the kernel. Then all values are summed up resulting in a scalar output. One example of a convolution operation is visualized in FIG. 5. Stacking multiple convolutional layers allows a network to learn more and higher level features. For example, in image processing the first convolution layers learn edges and corners, and then later layers learn full objects. By way of example, in FIG. 5 a 3×3 kernel is convolved over a 5×5 input (blue) zero padding and unit strides, resulting in the output (green).

Autoencoders

An autoencoder is a neural network that is trained to output a given input. Internally, it has a hidden layer h that describes a code used to represent the input. The network may be viewed as comprising two parts: an encoder function $h=f(x)$, and a decoder that produces a reconstruction $r=g(h)$. Undercomplete autoencoders constrain h to have a smaller dimension than x. Learning an undercomplete representation forces the autoencoder to capture the most salient features of the training data. The learning process may be described simply as minimizing a loss function $L(x,g(f(x)))$, where L is a loss function penalizing $g(f(x))$ for being dissimilar from x. Regularized autoencoders provide the ability to train an autoencoder which fulfills other properties besides reconstructing the input.

Autoencoders exploit the idea that data concentrates around a low-dimensional manifold or a small set of such manifolds. Autoencoders are configured to learn the structure of a manifold. An important characterization of a manifold is the set of its tangent planes. At a point x on a d-dimensional manifold, the tangent plane is given by d basis vectors that span the local directions of variation allowed on the manifold. These local directions specify how one can change x infinitesimally while staying on the manifold.

All autoencoder training procedures involve a compromise between two terms of a cost function:
1. Learning a representation h of a training example x, so that x can be approximately recovered from h through a decoder.
2. Satisfying the latent constraint or regularization penalty.

The underlying idea is that the two terms together force the hidden representation to capture information about the structure of the input data. An important principle is that an autoencoder can afford to represent only the variations that are needed to reconstruct training examples. If the input data concentrates near a low-dimensional manifold, this yields representations that implicitly capture a local coordinate system for the manifold: only the variations tangent to the manifold around x need to correspond to changes in $h=f(x)$. Therefore, the encoder learns a mapping from the input space x to a representation space, a mapping that is only sensitive to changes along the manifold directions, but is insensitive to changes orthogonal to the manifold.

Discriminative Training Machine Learning Models

A discriminative training (DT) machine learning model (or MLM) works in combination with a loss or cost function module (or LM). The DT MLM is configured to provide its results or predictions to the LM, and in turn the LM is configured to provide outputs based on the DT MLM's results or predictions back to the DT MLM (more about which is said below). The DT MLM can be any suitable type of machine learning module or network, such as one or more of the following types of networks or modules: convolutional neural network (CNN), decision tree, support vector machine, logistic regression, mixture of Gaussian, a feedforward neural network or artificial neuron network, a radial basis function neural network, a Kohonen self-organizing neural network, a recurrent neural network (RNN) or long short term memory network, and/or a modular neural network. The DT MLM and/or the LM can also be configured to employ optimization techniques or schemes such as stochastic gradient descent schemes or decision tree schemes.

An input signal x to a machine learning model DT may comprises data recorded from catheter or medical device 110 electrodes BS (x). In some embodiments, signal x potentially undergoes preprocessing steps, such as a high/low/band-pass filtering. The desired output(s) y of the machine learning model provides an estimate(s) for one or more properties of the constant current signals detected in the patient's heart 10. Training data (x, y) can be obtained from simultaneous recordings from body surface electrodes (x) and intracardiac electrodes (y). In one embodiment, the machine learning model is parametrized with parameters W. These can be weights of neural network connections, etc.

The prediction of the machine learning model is then $\hat{y}=fW(x)$ (or "f of x, parametrized by W"). This prediction should be as close as possible to y. During training, parameters W are optimized so as to minimize the error in estimating y. Such an error can be described as a loss function $L(y, \hat{y})$, for example the modulus of the difference $L(y, \hat{y})=\|y-\hat{y}\|$. Which is carried out in block LM, as described above.

A DT MLM can be trained to directly predict electrode positions using sensed electrical signal values and expected electrical signal values corresponding thereto, thereby to provide subsequent three-dimensional locations of the catheter or medical device electrodes located within patient's body 5 and the at least portion of the volume during each or selected ones of the subsequent given periods of time, thereby to permit navigation, positioning and/or imaging of the catheter or medical device 100, or portion thereof, inside patient's body 5.

After having read and understood the present specification, drawings and claims, those skilled in the art will now understand that configurations and architectures of MLMs other than those explicitly described and disclosed herein can also be used obtain similarly useful results.

FIG. 23 shows a table comparing various different types of well-known medical navigation systems, in addition to the controlled constant current navigation system (Ablamap CS-Navigation system) described and disclosed herein. Such systems, in addition to the controlled constant current navigation system described and disclosed herein include the Carto system, the Ensite system, the Rhythmia system, the Affera system, the NavX system the Acutus system, and the CardioNXT system. Reference to FIG. 23 will show that in addition to the much lower cost of the controlled constant current navigation system described and disclosed herein, the Ablamap CS-Navigation system delivers very high positional accuracy (within 1 mm in some embodiments), high reproducibility precision (+ or −1 mm in some embodiments, low levels of map shift, no triangulation errors, low hardware complexity, excellent state-of-the-art real-time 3D visualization, and the ability to use standard catheters already in widespread use. The Ablamap CS-Navigation system (or controlled constant current navigation, positioning and imaging system) described and disclosed herein has many advantages and overcomes many hurdles and difficulties presented by prior art navigation system, including, but not limited to, significantly lower system cost, increased ease of use, improved accuracy, and faster real-time results.

Further embodiments of medical navigation systems will become apparent to those skilled in the art after having read and understood the claims, specification and drawings hereof.

It will now be seen that the various systems, devices, components and methods disclosed and described herein are capable of permitting a medical device to be navigated, positioned and imaged inside a human body quickly, and with considerable accuracy and precision, thereby permitting the delivery of better informed and more accurate and likely-to-succeed treatment decisions for patients.

In view of the structural and functional descriptions provided herein, those skilled in the art will appreciate that portions of the described devices and methods may be configured as methods, data processing systems, or computer methods. Accordingly, these portions of the devices and methods described herein may take the form of a hardware embodiment, a software embodiment, or an embodiment combining software and hardware, such as shown and described with respect to computer system 300 illustrated in FIG. 2. Furthermore, portions of the devices and methods described herein may be a computer method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer methods. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

In this regard, FIG. 2 illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto (in addition to navigation, positioning and imaging modalities). Likewise, systems 100 shown in FIGS. 1, 3, 18 and 19 may be modified to permit the acquisition of both body surface and intra-cardiac electrode data simultaneously or sequentially.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of the systems, devices, components and methods described and disclosed herein fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, claims, and drawings set forth herein, those skilled in the art will now understand and appreciate that the various embodiments described herein provide solutions to long-standing problems, in the use of medical navigation systems, electrophysiological mapping systems, and cardiac ablation systems.

We claim:

1. A method of at least one of navigating and positioning a catheter inside a patient's body using: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough; and (d) a data acquisition or recording device operably connected to at least one computing device, the data acquisition or recording device being operably connected to the catheter electrodes and configured to acquire, or store or record, electrical signals corresponding to transmitted controlled constant current signals sensed by at least some of the plurality of catheter electrodes as sensed electrical signals, the data acquisition or recording device further being configured to relay the sensed electrical signals to the at least one computing device as sensed electrical signal values, the at least one computing device comprising at least one non-transitory computer readable medium configured to store instructions executable by at least one processor to permit navigation or positioning of the catheter inside the patient's body, the method comprising:

using the at least one computing device, generating at least one three-dimensional model or matrix of a volume of a portion of the patient's body through or into which the catheter is to be navigated or positioned, the volume comprising a plurality of voxels, each voxel having a three-dimensional spatial coordinate within the volume;

using the at least one computing device, and for each voxel or selected ones of the voxels, generating expected electrical signal values corresponding to controlled constant current signals transmitted from the body surface electrodes to each voxel or selected ones of the voxels;

positioning and operably coupling the plurality of body surface electrodes on or to the first portion of the patient's body surface;

positioning the catheter or a portion thereof inside the patient's body and within at least a portion of the volume;

delivering, over a given period of time, the controlled constant current signals to the plurality or selected ones of the body surface electrodes for transmission into at least portions of the volume;

using the data acquisition or recording device and the at least one computing device, acquiring the sensed electrical signals from the plurality or selected ones of the catheter electrodes during the given period of time, and storing or recording sensed electrical signal values corresponding to the sensed electrical signals, the sensed electrical signals corresponding to controlled constant current signals transmitted by the plurality or selected ones of the body surface electrodes into at least portions of the volume during the given period of time, and using the at least one computing device, and for at least a portion of the given period of time, on the basis of the sensed electrical signal values and the expected electrical signal values corresponding thereto and using controlled constant current signals sensed by or transmitted from a coronary sinus catheter to compensate for at least one of (i) movements of the patient's atria with heartbeat, (ii) movements resulting from the patient breathing, and (iii) other patient movements, determining at least one three-dimensional location of at least one of the catheter electrodes located within the patient's body and the at least portion of the volume during the given period of time.

2. The method of claim 1, wherein following the given period of time, and during subsequent given periods of time, continuing to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and expected electrical signal values corresponding thereto, subsequent three-dimensional locations of the at least of the catheter electrodes located within the patient's body and the at least portion of the volume during each or selected ones of the subsequent given periods of time, thereby to permit navigation or positioning of the catheter or the portion thereof inside the patient's body.

3. The method of claim 1, wherein the at least one three-dimensional location of at least one of the catheter electrodes is located within the patient's heart, and further wherein the at least portion of the volume is located within the patient's heart.

4. The method of claim 3, further comprising sensing cardiac electrical signals from the patient's heart, determining at least one shape of the patient's QRS complex from the cardiac electrical signals, and verifying or improving the accuracy of the determination of the at least one three-dimensional location.

5. The method of claim 3, further comprising, using the sensed electrical signals, reconstructing and displaying a geometry or visual model of the catheter.

6. The method of claim 3, further comprising, using the sensed electrical signals, generating an anatomical shell representation of at least a portion of an interior the patient's heart and displaying the anatomical shell representation.

7. The method of claim 1, wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter.

8. The method of claim 1, wherein at least some of the plurality of catheter electrodes comprise one or more of sensing electrodes, ablation electrodes, electrophysiological (EP) mapping electrodes, and navigation electrodes.

9. The method of claim 1, wherein at least one corresponding ground electrode for use in conjunction with the plurality of body surface electrodes is provided.

10. The method of claim 9, wherein the at least one ground electrode is configured for placement on or over a second portion of the patient's body surface.

11. The method of claim 1, wherein the at least one controlled constant current source is configured to adjust the voltage and/or current at each body surface electrode to compensate for undesired variations in resistance or impedance at the skin-electrode interface.

12. The method of claim 11, wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape.

13. The method of claim 1, wherein the at least one controlled constant current source is at least one of an alternating current (AC) source and a direct current (DC) source.

14. The method of claim 1, wherein the at least one controlled constant current source is configured to deliver controlled constant current AC signals having frequencies ranging between about 1 kHz and about 1 MHz.

15. The method of claim 14, wherein the at least one controlled constant current source is further configured to generate and deliver controlled constant current AC signals having amplitudes ranging between about 0.1 mA and about 100 mA.

16. The method of claim 1, wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source.

17. The method of claim 1, wherein the at least one controlled constant current source is further configured to be sequentially connected to the plurality of body surface electrodes and to deliver sequentially controlled constant current signals thereto.

18. The method of claim 1, wherein the at least one controlled constant current source is further configured to be sequentially connected to each of the plurality of body surface electrodes between about once every 10 milliseconds and about once every 500 milliseconds.

19. The method of claim 1, wherein the at least one controlled constant current source is further configured to be sequentially connected to each of the plurality of body surface electrodes between about once every 100 milliseconds and once about every 300 milliseconds.

20. The method of claim 1, wherein the data acquisition or recording device further comprises amplifiers and filters configured to amplify and filter the sensed electrical signals.

21. The method of claim 20, wherein the amplifiers and filters are configured to at least one of amplify, bandpass filter, notch filter, low-pass filter, high pass filter, and digitally filter the sensed electrical signals.

22. The method of claim 1, wherein the at least one three-dimensional location of at least one of the catheter electrodes located within the patient's body and the at least portion of the volume is determined with an accuracy of about 2 mm or less.

23. The method of claim 1, wherein a number of the plurality of body surface electrodes ranges at least one of between 2 and 128, between 4 and 32, between 1 and 256, or between 8 and 64 electrodes.

24. The method of claim 1, wherein the at least one three-dimensional model or matrix of the volume is generated according to at least one of the patient's body mass index (BMI), sex, weight, size, and age.

25. The method of claim 1, wherein the catheter is configured to be inserted into a patient's vein or artery and moved therethrough or therein.

26. The method of claim 25, wherein the catheter is configured to be inserted into one of a patient's coronary artery, brain, throat, esophagus, stomach, liver, urinary tract, colon, orifice, or other body organ, tissue or passageway.

27. A system configured to navigate or position a catheter inside a patient's body, the system comprising:

(a) a plurality of body surface electrodes, the body surface electrodes being configured for placement on or over a first portion of the patient's body surface;

(b) a plurality of catheter electrodes mounted on or attached to the catheter, each catheter electrode having a predetermined location or position on or in the catheter;

(c) at least one controlled constant current source configured to be operably connected to the plurality or selected ones of the body surface electrodes and to transmit controlled constant current signals therethrough into the patient's body; and (d) a data acquisition or recording device operably connected to at least one computing device and the catheter electrodes, and configured to acquire, or store or record, electrical signals corresponding to transmitted controlled constant current signals sensed by at least some of the plurality of catheter electrodes as sensed electrical signals, the data acquisition or recording device being further configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, inside the patient's body;

wherein:

(a) the at least one computing device is further configured to:

(i) generate at least one three-dimensional model or matrix of a volume of a portion of the patient's body through or into which the catheter is to be navigated or positioned, the volume comprising a plurality of voxels, each voxel having a three-dimensional spatial coordinate within the volume; and (ii) for each voxel or selected ones of the voxels, generate expected electrical signal values corresponding to controlled constant current signals transmitted from the body surface electrodes to each voxel or selected ones of the voxels;

(b) the controlled constant current source is further configured to deliver, over a given period of time, the controlled constant current signals to the plurality or selected ones of the body surface electrodes for transmission into at least portions of the volume;

(c) the data acquisition or recording device and the at least one computing device are configured to acquire the sensed electrical signals from the plurality or selected ones of the catheter electrodes during the given period of time, or store or record, sensed electrical signal values corresponding to the sensed electrical signals, the sensed electrical signals corresponding to controlled constant current signals transmitted by the plurality or selected ones of the body surface electrodes into at least portions of the volume during the given period of time, and (d) the at least one computing device is configured to, for at least a portion of the given period of time, on the basis of the sensed electrical signal values and the expected electrical signal values corresponding thereto and using controlled constant current signals sensed by or transmitted from a coronary sinus catheter to compensate for at least one of (i) movements of the patient's atria with heartbeat, (ii) movements resulting from the patient breathing, and (iii) other patient movements, determine at least one three-dimensional location of at least one of the catheter electrodes located within the patient's body and the at least portion of the volume during the given period of time.

28. The system of claim 27, further comprising the system being configured to sense cardiac electrical signals from the patient's heart, determine at least one shape of the patient's QRS complex from the cardiac electrical signals, and verify or improve the accuracy of the determination of the at least one three-dimensional location.

29. The system of claim 27, further comprising the system being configured to use the sensed electrical signals to reconstruct and display a geometry or visual model of the catheter.

30. The method of claim 27, further comprising the system being configured to, use the sensed electrical signals, generate an anatomical shell representation of at least a portion of an interior the patient's heart, and display the anatomical shell representation.

31. The system of claim 27, wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter.

32. The system of claim 27, wherein at least some of the plurality of catheter electrodes comprise one or more of sensing electrodes, ablation electrodes, electrophysiological (EP) mapping electrodes, and navigation electrodes.

33. The system of claim 27, further comprising at least one corresponding ground electrode for use in conjunction with the plurality of body surface electrodes.

34. The system of claim 33, wherein the at least one ground electrode is configured for placement on or over a second portion of the patient's body surface.

35. The system of claim 27, wherein the at least one controlled constant current source is configured to adjust the voltage and/or current at each body surface electrode to compensate for undesired variations in resistance or impedance at the skin-electrode interface.

36. The system of claim 27, wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape.

37. The system of claim 27, wherein the at least one controlled constant current source is at least one of an alternating current (AC) source and a direct current (DC) source.

38. The system of claim 27, wherein the at least one controlled constant current source is configured to deliver constant current AC signals ranging between about 1 kHz and about 1 MHz.

39. The system of claim 38, wherein the at least one controlled constant current source is further configured to generate and deliver constant current AC signals having amplitudes ranging between about 0.1 mA and about 100 mA.

40. The method of claim 27, wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source.

41. The system of claim 27, wherein the at least one controlled constant current source is further configured to be sequentially connected to the plurality of body surface electrodes and to deliver sequentially controlled constant current signals thereto.

42. The system of claim 27, wherein the at least one controlled constant current source is further configured to be sequentially connected to each of the plurality of body surface electrodes between about once every 10 milliseconds and about once every 500 milliseconds.

43. The system of claim 27, wherein the at least one controlled constant current source is further configured to be sequentially connected to each of the plurality of body surface electrodes between about once every 100 milliseconds and once about every 300 milliseconds.

44. The system of claim 27, wherein the data acquisition or recording device further comprises amplifiers and filters configured to amplify and filter the sensed electrical signals.

45. The system of claim 44, wherein the amplifiers and filters are configured to at least one of amplify, bandpass filter, notch filter, low-pass filter, high pass filter, and digitally filter the sensed electrical signals.

46. The system of claim 27, wherein the system is further configured to permit the at least one three-dimensional location of at least one of the catheter electrodes located within the patient's body and the at least portion of the volume to be determined with an accuracy of about 2 mm or less.

47. The system of claim 27, wherein a number of the plurality of body surface electrodes ranges at least one of between 2 and 128, between 4 and 32, between 1 and 256, or between 8 and 64 electrodes.

48. The system of claim 27, wherein the at least one computing device is further configured to generate the at least one three-dimensional model or matrix of the volume according to at least one of the patient's body mass index (BMI), sex, weight, size, and age.

49. The system of claim 27, wherein the catheter is configured to be inserted into a patient's vein or artery and moved therethrough or therein.

50. The system of claim 27, wherein the catheter is configured to be inserted into one of a patient's coronary artery, brain, throat, esophagus, stomach, liver, urinary tract, colon, orifice, or other body organ, tissue or passageway.

51. A method of at least one of navigating and positioning a catheter inside a patient's body using: (a) a plurality of body surface electrodes, the body surface electrodes being configured for placement on or over a first portion of the patient's body surface; (b) a plurality of catheter electrodes mounted on or attached to the catheter, each catheter electrode having a predetermined location or position on or in the catheter; (c) at least one controlled constant current source configured to be operably connected to the plurality or selected ones of the body surface electrodes and to transmit controlled constant current signals therethrough; and (d) a data acquisition or recording device operably connected to at least one computing device, the data acquisition or recording device being operably connected to the catheter electrodes and configured to acquire, or store or record, electrical signals corresponding to transmitted controlled constant current signals sensed by at least some of the plurality of catheter electrodes as sensed electrical signals, the data acquisition or recording device further being configured to relay the sensed electrical signals to the at least one computing device as sensed electrical signal values, the at least one computing device comprising at least one non-transitory computer readable medium configured to store instructions executable by at least one processor to permit navigation or positioning of the catheter inside the patient's body, the method comprising:

positioning and operably coupling the plurality of body surface electrodes on or to the first portion of the patient's body surface;

positioning the catheter or a portion thereof inside the patient's body and within at least a portion of the volume;

delivering, over a given period of time, the controlled constant current signals to the plurality or selected ones of the body surface electrodes for transmission into at least portions of the volume;

using the data acquisition or recording device and the at least one computing device, acquiring the sensed electrical signals from the plurality or selected ones of the catheter electrodes during the given period of time, and storing or recording sensed electrical signal values corresponding to the sensed electrical signals, the sensed electrical signals corresponding to controlled constant current signals transmitted by the plurality or selected ones of the body surface electrodes into at least portions of the volume during the given period of time, and using the at least one computing device, and for at least a portion of the given period of time, on the basis of the sensed electrical signal values and using controlled constant current signals sensed by or transmitted from a coronary sinus catheter to compensate for at least one of (i) movements of the patient's atria with heartbeat, (ii) movements resulting from the patient breathing, and (iii) other patient movements, computing and solving optimization problems to determine at least one three-dimensional location of at least one of the catheter electrodes located within the patient's body and the at least portion of the volume during the given period of time.

52. The method of claim 51, wherein following the given period of time, and during subsequent given periods of time, continuing to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and solving optimization problems to determine the three-dimensional locations corresponding to the sensed electrical signals and their respective catheter electrodes during the subsequent given periods of time, subsequent three-dimensional locations of the at least of the catheter electrodes located within the patient's body and the at least portion of the volume during each or selected ones of the subsequent given periods of time, thereby to permit navigation or positioning of the catheter or the portion thereof inside the patient's body.

53. The method of claim 51, further comprising using controlled constant current signals sensed by or transmitted from a coronary sinus catheter to compensate for at least one of movements of the patient's atria with heartbeat, movements resulting from the patient breathing, and other patient movements.

54. The method of claim 51, further comprising sensing cardiac electrical signals from the patient's heart, determining at least one shape of the patient's QRS complex from the cardiac electrical signals, and verifying or improving the accuracy of the determination of the at least one three-dimensional location.

55. The method of claim 51, further comprising, using the sensed electrical signals, reconstructing and displaying a geometry or visual model of the catheter.

56. The method of claim 51, further comprising, using the sensed electrical signals, generating an anatomical shell representation of at least a portion of an interior the patient's heart and displaying the anatomical shell representation.

57. The method of claim 51, wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter.

58. The method of claim 51, wherein at least some of the plurality of catheter electrodes comprise one or more of sensing electrodes, ablation electrodes, electrophysiological (EP) mapping electrodes, and navigation electrodes.

59. The method of claim 51, wherein at least one corresponding ground electrode for use in conjunction with the plurality of body surface electrodes is provided.

60. The method of claim 59, wherein the at least one ground electrode is configured for placement on or over a second portion of the patient's body surface.

61. The method of claim 51, wherein the at least one controlled constant current source is configured to adjust the voltage and/or current at each body surface electrode to compensate for undesired variations in resistance or impedance at the skin-electrode interface.

62. The method of claim 51, wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape.

63. The method of claim 51, wherein the at least one controlled constant current source is at least one of an alternating current (AC) source and a direct current (DC) source.

64. The method of claim 51, wherein the at least one controlled constant current source is configured to deliver constant current AC signals ranging between about 1 kHz and about 1 MHz.

65. The method of claim 51, wherein the at least one controlled constant current source is further configured to generate and deliver constant current AC signals having amplitudes ranging between about 0.1 mA and about 100 mA.

66. The method of claim 51, wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source.

67. The method of claim 51, wherein the at least one controlled constant current source is further configured to be sequentially connected to the plurality of body surface electrodes and to deliver sequentially controlled constant current signals thereto.

68. The method of claim 51, wherein the at least one controlled constant current source is further configured to be sequentially connected to each of the plurality of body surface electrodes between about once every 10 milliseconds and about once every 500 milliseconds.

69. The method of claim 51, wherein the at least one controlled constant current source is further configured to be sequentially connected to each of the plurality of body surface electrodes between about once every 100 milliseconds and once about every 300 milliseconds.

70. The method of claim 51, wherein the data acquisition or recording device further comprises amplifiers and filters configured to amplify and filter the sensed electrical signals.

71. The method of claim 70, wherein the amplifiers and filters are configured to at least one of amplify, bandpass filter, notch filter, low-pass filter, high pass filter, and digitally filter the sensed electrical signals.

72. The method of claim 51, wherein the at least one three-dimensional location of at least one of the catheter electrodes located within the patient's body and the at least portion of the volume is determined with an accuracy of about 2 mm or less.

73. The method of claim 51, wherein a number of the plurality of body surface electrodes ranges at least one of between 2 and 128, between 4 and 32, between 1 and 256, or between 8 and 64 electrodes.

74. The method of claim 51, wherein the catheter is configured to be inserted into a patient's vein or artery and moved therethrough or therein.

75. The method of claim 74, wherein the catheter is configured to be inserted into one of a patient's coronary artery, brain, throat, esophagus, stomach, liver, urinary tract, colon, orifice, or other body organ, tissue or passageway.

76. A system configured to navigate or position a catheter inside a patient's body, the system comprising:

(a) a plurality of body surface electrodes, the body surface electrodes being configured for placement on or over a first portion of the patient's body surface;

(b) a plurality of catheter electrodes mounted on or attached to the catheter, each catheter electrode having a predetermined location or position on or in the catheter;

(c) at least one controlled constant current source configured to be operably connected to the plurality or selected ones of the body surface electrodes and to transmit controlled constant current signals therethrough into the patient's body; and (d) a data acquisition or recording device operably connected to at least one computing device and the catheter electrodes, and configured to acquire, or store or record, electrical signals corresponding to transmitted controlled constant current signals sensed by at least some of the plurality of catheter electrodes as sensed electrical signals, the data acquisition or recording device being further configured to relay the sensed electrical signals to the computing device as sensed electrical signal values, the at least one computing device comprising at least one non-transitory computer readable medium configured to store instructions executable by at least one processor to permit navigation or positioning of the catheter or other type of medical device, inside the patient's body;

wherein:

(a) the controlled constant current source is further configured to deliver, over a given period of time, the controlled constant current signals to the plurality or selected ones of the body surface electrodes for transmission into at least portions of the volume;

(b) the data acquisition or recording device and the at least one computing device are configured to acquire the sensed electrical signals from the plurality or selected ones of the catheter electrodes during the given period of time, or store or record, sensed electrical signal values corresponding to the sensed electrical signals, the sensed electrical signals corresponding to controlled constant current signals transmitted by the plurality or selected ones of the body surface electrodes into at least portions of the volume during the given period of time, and (c) the at least one computing device is configured to, for at least a portion of the given period of time, on the basis of the sensed electrical signal values and the expected electrical signal values corresponding thereto and using controlled constant current signals sensed by or transmitted from a coronary sinus catheter to compensate for at least one of (i) movements of the patient's atria with heartbeat, (ii) movements resulting from the patient breathing, and (iii) other patient movements, computing and solving optimization problems to determine at least one three-dimensional location of at least one of the catheter electrodes located within the patient's body and the at least portion of the volume during the given period of time.

77. The system of claim 76, wherein following the given period of time, and during subsequent given periods of time, the system is configured to: (a) transmit controlled constant current signals through the body surface electrodes into the patient's body and the at least portion of the volume; (b) acquire sensed electrical signals; (c) store or record sensed electrical signal values, and (d) determine, on the basis of the sensed electrical signal values and solving optimization problems to determine the three-dimensional locations corresponding to the sensed electrical signals and their respective catheter electrodes during the subsequent given periods of time, subsequent three-dimensional locations of the at least of the catheter electrodes located within the patient's body and the at least portion of the volume during each or selected ones of the subsequent given periods of time, thereby to permit navigation or positioning of the catheter or the portion thereof inside the patient's body.

78. The system of claim 76, further comprising sensing cardiac electrical signals from the patient's heart, determining at least one shape of the patient's QRS complex from the cardiac electrical signals, and verifying or improving the accuracy of the determination of the at least one three-dimensional location.

79. The system of claim 76, further comprising, using the sensed electrical signals, reconstructing and displaying a geometry or visual model of the catheter.

80. The system of claim 76, further comprising, using the sensed electrical signals, generating an anatomical shell representation of at least a portion of an interior the patient's heart and displaying the anatomical shell representation.

81. The system of claim 76, wherein the catheter is one of a basket catheter, an electrophysiological mapping catheter, a lasso catheter, a fan-shaped catheter, an umbrella-shaped catheter, a pulsed field ablation (PFA) catheter, a coronary sinus catheter, and an ablation catheter.

82. The system of claim 76, wherein at least some of the plurality of catheter electrodes comprise one or more of sensing electrodes, ablation electrodes, electrophysiological (EP) mapping electrodes, and navigation electrodes.

83. The system of claim 76, wherein at least one corresponding ground electrode for use in conjunction with the plurality of body surface electrodes is provided.

84. The system of claim 82, wherein the at least one ground electrode is configured for placement on or over a second portion of the patient's body surface.

85. The system of claim 76, wherein the at least one controlled constant current source is configured to adjust the voltage and/or current at each body surface electrode to compensate for undesired variations in resistance or impedance at the skin-electrode interface.

86. The system of claim 76, wherein the body surface electrodes are configured in an array, and the array is configured in at least one of a cross shape, a triangular shape, a strip or linear shape, a plurality of strips or linear shapes, a square shape, a rectangular shape, a star shape, a round shape, an oval shape, an elliptical shape, a geometrically irregular shape, and a geometrically regular shape.

87. The system of claim 76, wherein the at least one controlled constant current source is at least one of an alternating current (AC) source and a direct current (DC) source.

88. The system of claim 76, wherein the at least one controlled constant current source is configured to deliver constant current AC signals ranging between about 1 kHz and about 1 MHz.

89. The system of claim 76, wherein the at least one controlled constant current source is further configured to generate and deliver constant current AC signals having amplitudes ranging between about 0.1 mA and about 100 mA.

90. The system of claim 76, wherein the at least one controlled constant current source is further configured to generate and deliver controlled constant current AC signals to the plurality of body surface electrodes such that each body surface electrode receives from the at least one controlled constant current source a controlled constant current AC signal having at least one of a frequency, a phase and an amplitude that is different from the frequencies, phases and/or amplitudes of the controlled constant current AC signals received by the other body surface electrodes from the controlled constant current source.

91. The system of claim 76, wherein the at least one controlled constant current source is further configured to be sequentially connected to the plurality of body surface electrodes and to deliver sequentially controlled constant current signals thereto.

92. The system of claim 76, wherein the at least one controlled constant current source is further configured to be sequentially connected to each of the plurality of body surface electrodes between about once every 10 milliseconds and about once every 500 milliseconds.

93. The system of claim 76, wherein the at least one controlled constant current source is further configured to be sequentially connected to each of the plurality of body surface electrodes between about once every 100 milliseconds and once about every 300 milliseconds.

94. The system of claim 76, wherein the data acquisition or recording device further comprises amplifiers and filters configured to amplify and filter the sensed electrical signals.

95. The system of claim 94, wherein the amplifiers and filters are configured to at least one of amplify, bandpass filter, notch filter, low-pass filter, high pass filter, and digitally filter the sensed electrical signals.

96. The system of claim 76, wherein the at least one three-dimensional location of at least one of the catheter electrodes located within the patient's body and the at least portion of the volume is determined with an accuracy of about 2 mm or less.

97. The system of claim 76, wherein a number of the plurality of body surface electrodes ranges at least one of between 2 and 128, between 4 and 32, between 1 and 256, or between 8 and 64 electrodes.

98. The system of claim 76, wherein the catheter is configured to be inserted into a patient's vein or artery and moved therethrough or therein.

99. The system of claim 76, wherein the catheter is configured to be inserted into one of a patient's coronary artery, brain, throat, esophagus, stomach, liver, urinary tract, colon, orifice, or other body organ, tissue or passageway.

* * * * *